United States Patent
Zhou

(10) Patent No.: US 9,400,169 B2
(45) Date of Patent: Jul. 26, 2016

(54) APPARATUS AND METHOD FOR SPACE-DIVISION MULTIPLEXING OPTICAL COHERENCE TOMOGRAPHY

(71) Applicant: Chao Zhou, Bethlehem, PA (US)

(72) Inventor: Chao Zhou, Bethlehem, PA (US)

(73) Assignee: LEHIGH UNIVERSITY

( * ) Notice: Subject to any disclaimer, the term of this patent is extended or adjusted under 35 U.S.C. 154(b) by 64 days.

(21) Appl. No.: 14/002,523

(22) PCT Filed: Jul. 24, 2013

(86) PCT No.: PCT/US2013/051883
§ 371 (c)(1),
(2) Date: Aug. 30, 2013

(87) PCT Pub. No.: WO2014/088650
PCT Pub. Date: Jun. 12, 2014

(65) Prior Publication Data
US 2014/0160488 A1    Jun. 12, 2014

Related U.S. Application Data

(60) Provisional application No. 61/734,168, filed on Dec. 6, 2012, provisional application No. 61/819,251, filed on May 3, 2013.

(51) Int. Cl.
*G01B 9/02* (2006.01)
*A61B 5/00* (2006.01)

(52) U.S. Cl.
CPC .......... *G01B 9/02091* (2013.01); *A61B 5/0066* (2013.01); *G01B 9/02004* (2013.01); *G01B 9/02019* (2013.01); *G01B 9/02028* (2013.01)

(58) Field of Classification Search
CPC .......... G01B 9/02004; G01B 9/02019; G01B 9/02028; G01B 9/02091; A61B 5/0066
See application file for complete search history.

(56) References Cited

U.S. PATENT DOCUMENTS

| | | | |
|---|---|---|---|
| 7,126,693 B2 | 10/2006 | Everett et al. | |
| 7,256,894 B2 | 8/2007 | Chen et al. | |

(Continued)

FOREIGN PATENT DOCUMENTS

| | | |
|---|---|---|
| JP | 2009008393 A | 1/2009 |
| WO | 2012121999 | 9/2012 |

(Continued)

OTHER PUBLICATIONS

Zhou, Chao et al. "Photothermal optical coherence tomography in ex vivo human breast tissues using gold nanoshells". Optics Letters, vol. 35, No. 5, Mar. 1, 2010, pp. 700-702.*

(Continued)

*Primary Examiner* — Michael A Lyons
(74) *Attorney, Agent, or Firm* — The Belles Group, P.C.

(57) ABSTRACT

A space-division multiplexing optical coherence tomography apparatus and system is provided. In one embodiment, the system includes a light source, a reference arm, and a sample arm. The sample arm splits the sampling light into a plurality of sampling beams which may be scanned simultaneously onto a surface of a sample. An optical delay may be introduced into the sampling beams before scanning. A plurality of reflected light signals returned from the sample is collected. In one arrangement, the signals may be combined to produce a single reflected light signal. The reflected light signal(s) and a reference signal are combined to produce an interference signal comprising data representative of digitized images captured of the actual object. In one embodiment, a single sample arm may be used for scanning and collecting image data. A related method is also provided.

27 Claims, 18 Drawing Sheets

(56) References Cited

U.S. PATENT DOCUMENTS

| | | | |
|---|---|---|---|
| 7,355,721 | B2 | 4/2008 | Quadling et al. |
| 7,362,444 | B2 | 4/2008 | Izatt et al. |
| 7,391,520 | B2 | 6/2008 | Zhou et al. |
| 7,417,740 | B2 | 8/2008 | Alphonse et al. |
| 7,592,582 | B2 | 9/2009 | Mikuriya et al. |
| 7,630,083 | B2 | 12/2009 | De Boer et al. |
| 7,701,588 | B2* | 4/2010 | Chong ............ A61B 5/0066 356/497 |
| 7,708,408 | B1 | 5/2010 | Bor |
| 7,826,059 | B2 | 11/2010 | Roth et al. |
| 7,929,146 | B2 | 4/2011 | Izatt et al. |
| 7,940,398 | B2 | 5/2011 | Ohbayashi et al. |
| 8,175,685 | B2 | 5/2012 | Yun et al. |
| 8,274,660 | B2 | 9/2012 | Sugita |
| 8,285,368 | B2 | 10/2012 | Chen et al. |
| 8,355,138 | B2 | 1/2013 | Yun et al. |
| 8,496,585 | B2 | 7/2013 | Lu |
| 2006/0103850 | A1* | 5/2006 | Alphonse ......... A61B 5/0066 356/479 |
| 2008/0204762 | A1 | 8/2008 | Izatt et al. |
| 2009/0036772 | A1 | 2/2009 | Lu |
| 2010/0284021 | A1 | 11/2010 | Hacker |
| 2011/0206291 | A1 | 8/2011 | Kashani et al. |
| 2011/0255095 | A1* | 10/2011 | Jiang et al. ............ 356/479 |
| 2012/0232821 | A1 | 9/2012 | Liu |
| 2012/0257210 | A1* | 10/2012 | Whitney et al. ........ 356/479 |
| 2012/0281724 | A1 | 11/2012 | Frisken |
| 2012/0327423 | A1 | 12/2012 | Hanebuchi |
| 2013/0162948 | A1 | 6/2013 | Yazdanfar et al. |
| 2013/0185023 | A1 | 7/2013 | Vakoc et al. |
| 2013/0201485 | A1 | 8/2013 | Rubio-Guivernau |

FOREIGN PATENT DOCUMENTS

| | | |
|---|---|---|
| WO | 2012122000 | 9/2012 |
| WO | 2012160005 | 11/2012 |

OTHER PUBLICATIONS

B. Baumann et. al, Swept source/ Fourier domain polarization sensitive optical coherence tomography with a passive polarization delay unit. Optics Express, Apr. 23, 2012, pp. 10,218-10,230, vol. 20, No. 9.

H. Hendargo et. al., Depth-encoded spectral domain phase microscopy for simultaneous muti-site nanoscale optical measurements, Optics Communcication, Jun. 15, 2011.

B. Standish. et al., In vivo endoscopic multi-beam optical coherence tomography, Iopscience, Jan. 13, 2010.

N. Suehira et. al., Three-beam spectral-domain optical coherence tomography for retinal imagaing, Journal of BioMedical Optics, Nov. 5, 2012.

W. Wieser et. al., Multi-Megahertz OCT: High quality 3D imaging at 20 million A-scans and 4.5 GVoxels per second, Optics Express, Jul. 5, 2010, pp. 14,685-14,704, vol. 18, No. 14.

D. Adler et al., Extended coherence length Fourier domain mode locked lazers at 1310 nm, Optics Express, Oct. 10, 2011, pp. 20930-20939, vol. 19, No. 21.

A.D. Aguirre et al., High-resolution optical coherence microscopy for high-speed, in vivo cellular imaging, Optics Letters, Nov. 1, 2003, vol. 28, No. 21.

A. Bachmann et al., Dual beam heterodyne Fourier domain optical coherence tomography, Optics Express, Jul. 23, 2007, pp. 9254-9266, vol. 15, No. 15.

Riuiyi Chen et al., A Proposal of Zero Leakage-Loss Passive Optical Combiner Based on Nonreciprocal Waveguide, IEEE Photonics Technology Letters, Oct. 15, 2009, pp. 1493-1495. vol. 21, No. 20.

WooJhon Choi et al., Phase-sensitive swept-source optical coherence tomography imaging of the human retina with a vertical cavity surface-emitting laser light source, Feb. 1, 2013, pp. 336-340, vol. 38, No. 3.

Michael A. Choma et al., Sensitivity advantage of swept source and Fourier domain optical coherence tomography, Optics Express, Sep. 8, 2003, pp. 2183-2189, vol. 11, No. 18.

N.J. Curtis et al., Morphology of the Pupal Heart, Adult Heart, and Associated Tissues in the Fruit Fly, *Drosophila melanogaster*, Journal of Morphology, pp. 225-235, 1999.

Johannes F. De Boer et al., Improved signal-to-noise ratio in spectral-domain compared with time-domain optical coherence tomography, Optics Letters, Nov. 1, 2003, pp. 2067-2069, vol. 28. No. 21.

Wolfgang Drexler et al., Ultra-high-resolution ophthalmic optical coherence tomography, Nature Medicine, Apr. 2001, pp. 502-507, vol. 7, No. 4.

James G Fujimoto, Optical Coherence tomography for ultrahigh resolution in vivo imaging, Nature Biotechnology, Nov. 2003, pp. 1381-1367, vol. 21, No. 11.

Ireneusz Grulkowski et al., High-precision, high-accuracy ultralong-range swept-source optical coherence tomography using vertical cavity surface emitting laser light source, Optics Letters, Mar. 1, 2013. pp. 673-675, vol. 38, No. 5.

Ireneusz Grulkowski et al., Retinal, anterior segment and full eye imaging using ultrahigh speed swept source OCT with vertical-cavity surface emitting lasers, Biomedical Optics Express, Nov. 1, 2012, pp. 2733-2751, vol. 3, No. 11.

Robert Huber et al., Buffered Fourier domain mode locking: unidirectional swept laser sources for optical coherence tomorgraphy imaging at 370,000 lines/s, Optics Letters, Oct. 15, 2006, pp. 2976-2977, vol. 31, No. 20.

R. Huber et al., Fourier Domain Mode Looking (FDML): A new laser operating regime and applications for optical coherence tomography, Optics Express, Apr. 17, 2006, pp. 3225-3237, vol. 14. No. 8.

Joseph A. Izatt et al., Optical coherence microscopy in scattering media, Optics Letters, Apr. 15, 1994. pp. 590-592, vol. 19, No. 8.

V. Jayaraman et al., OCT Imaging up to 760 kHz Axial Scan Rate Using Single-Mode 1310nm MEMS-Tunable VCSELs with >100nm Tuning Range, OSA/CLEO 2011.

R. Leitgeb et al., Performance of former domain vs. time domain optical coherence tomography, Optics Express, Apr. 21, 2003, pp. 889-894, vol. 11, No. 8.

Airong Li et al., Changes in the Expression or the Alzheimer's Diaease-Associated Presenilin Gene in *Drosophila* Heart Leads to Cardiac Dysfunction, Current Alzheimer Research, 2011, pp. 1-10, vol. 8, No. 1.

Benjamin Potsaid et al., Ultrahigh speed 1050nm swept source / Fourier domain OCT retinal and anterior segment imaging at 100,000 to 400,000 axial scans per second, Optics Express, Sep. 13, 2010, pp. 20029-20048. vol. 18, No. 19.

Ye Tao et al., Heart development in *Drosophila*, Seminars in Cell & Developmental Biology, Dec. 5, 2006, pp. 3-15.

J. J. G. M. Van Der Tol et al., A Mach-Zehnder-Interferometer-Based Low-Loss Combiner, IEEE Photonics Technology Letters, Nov. 2001, pp. 1197-1199, vol. 13, No. 11.

Wolfgang Wieser et al., Extended coherence length megahertz FDML and its application for anterior segment imaging, Biomedical Optics Express, Oct. 1, 2012, pp. 2647-2657, vol. 3, No. 10.

Chao Zhou et al., Integrated Optical Coherence Tomography and Microscopy for Ex Vivo Multiscale Evaluation of Human Breast Tissues, Cancer Research, www.aacrjournals.org, Nov. 5, 2010.

Stefan Zotter et al., Visualization of microvasculature by dual-beam phase-resolved Doppler optical coherence tomography, Optics Express, Jan. 17, 2011, pp. 1217-1227, vol. 19, No. 2.

Corresponding International Search Report and Written Opinion dated Dec. 30, 2013.

International Search Report and Written Opinion of the International Searching Authority, PCT International Application No. PCT/US2013,73704, mailed Apr. 18, 2014. WO.

* cited by examiner

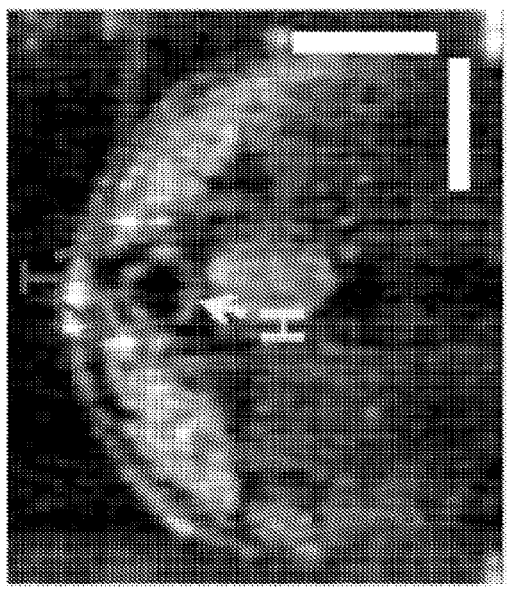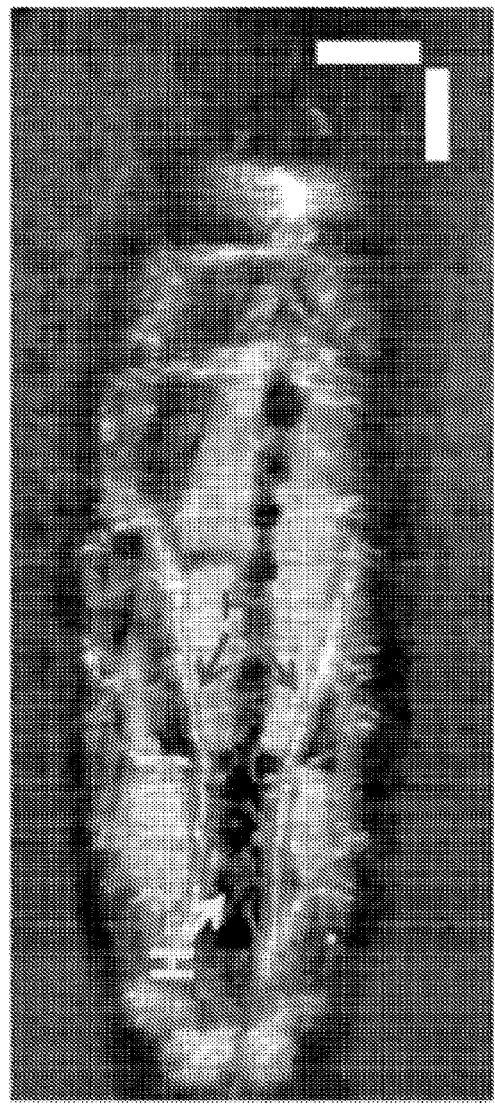
FIG. 9

APPARATUS AND METHOD FOR SPACE-DIVISION MULTIPLEXING OPTICAL COHERENCE TOMOGRAPHY

CROSS REFERENCE TO RELATED APPLICATIONS

The present application claims the benefit of priority to U.S. Provisional Patent Application No. 61/734,168 filed Dec. 6, 2012, and U.S. Provisional Patent Application No. 61/819,251 filed May 3, 2013; the contents of which are both incorporated herein by reference in their entireties.

STATEMENT OF GOVERNMENT INTEREST

This invention was made with government support under R00-EB010071 awarded by National Institutes of Health (NIH)-National Institute of Biomedical Imaging and Bioengineering (NIBIB). The government has certain rights in the invention.

FIELD OF DISCLOSURE

The present disclosure relates to tomography, and more particularly to optical coherence tomography.

BACKGROUND OF THE DISCLOSURE

Optical coherence tomography (OCT) is an emerging optical imaging technique that enables micron-scale, cross-sectional, and three-dimensional (3D) imaging of biological tissues in situ and in real-time. OCT functions as a type of "optical biopsy," imaging tissue microstructure with resolutions approaching that of standard histopathology, but without the need to remove and process tissue specimens. Accordingly, OCT captures and digitizes visual images of tangible objects such as biological tissue. The penetration depth of OCT is usually 1-2 mm in biological tissues. OCT has been used for a wide range of clinical and biomedical applications particularly in humans and animals, including ophthalmology, cardiovascular imaging, endoscopy imaging, cancer imaging, dental applications, and research imaging applications.

Current commercial ophthalmic OCT systems operate at 20-70 kHz. Each 3D scan covering 512×512 A-lines takes 3-10 seconds. Commercial cardiovascular and endoscopic OCT imaging systems operate at 100 kHz-200 kHz A-line rate in order to cover a large imaging field. Higher imaging speed at over 1 MHz A-line rate as a goal is ultimately desirable for faster imaging and less motion artifacts. However, currently there is no commercially-available wavelength tunable laser or high speed line-scan camera that operates at that speed. Imaging speeds for OCT, characterized as number of A-scans per second, is limited by the line rate of line-scan cameras for spectral-domain OCT (SD-OCT) or by the laser sweep rate for swept-source OCT (SS-OCT).

SUMMARY OF INVENTION

An optical coherence tomography (OCT) system is provided herein which improves imaging speed over the foregoing systems. In one exemplary embodiment, the system may be a space-division multiplexing (SDM) optical coherence tomography (SDM-OCT) system. In various embodiments, the SDM-OCT system may utilize a wavelength tunable light source such as a swept-source laser or a broadband light source. The SDM-OCT systems disclosed herein may map signals from spatially distributed sampling beams into different frequency bands using optical time delays.

An OCT system according to the present disclosure may be configured to take advantage of the long coherence length property of newly available light sources, such as without limitation, wavelength tunable lasers (e.g. vertical cavity surface-emitting laser, VCSEL) to improve imaging depth range. The OCT system may further utilize parallel detection of spatially distributed optical beams to achieve an order of magnitude improvement of effective A-line rate. Advantageously, this offers several fold improvement in imaging speed of OCT while maintaining resolution and sensitivity. In one embodiment, this may be achieved utilizing a single detection channel to obtain sample images, thereby enabling a simple, less complex, and less expensive OCT system to be provided with an effective imaging speed scalable to using a plurality of light sampling beams. In addition to dramatically improved imaging speed, the OCT system also preserves image resolution and enables synchronized simultaneous imaging at multiple different sample locations using multiple beams, which opens up opportunities for numerous biomedical applications.

In one embodiment, an optical coherence tomography system with space-division multiplexing is provided. The system includes: a light source producing light; a first optical device configured to split the light into reference light and sampling light; a second optical device configured to split the sampling light into a plurality of sampling beams; an optical delay element configured to produce an optical delay between the plurality of sampling beams; a scanner configured to simultaneously scan the plurality of sampling beams onto a surface of a sample; and a third optical device configured to generate an interference signal based on receiving reflected light signals returned from the surface of the sample produced by the plurality of sampling beams and the reference light. The interference signal includes data representing digitized images of the sample.

In another embodiment, an optical coherence tomography system with space-division multiplexing includes: a light source producing coherent light; a first optical device configured to divide the light into reference light and sampling light; a reference arm defining a first optical light path, the reference arm receiving the reference light and generating a reference light signal based on the reference light; a single sample arm defining a second optical light path and receiving the sampling light; an optical splitter arranged on the sample arm and configured to divide the sampling light into a plurality of sampling light beams; and an optical delay element configured to produce an optical delay between the plurality of sampling beams. The system is configured to simultaneously scan the plurality of sampling beams onto a surface of a sample. In one embodiment, the system includes a galvanometer scanner to scan the sampling beams. Other type scanners may be used. Also provided is a second optical device configured to receive and combine the reference light signal and a plurality of reflected light signals each returned from the surface of the sample produced by each of the plurality of sampling beams to produce an interference signal. The interference signal includes data representing digitized images of the sample.

In another embodiment, a low insertion loss optical coherence tomography system with space-division multiplexing includes: a light source producing coherent light; an optical device configured to divide the light into reference light and sampling light; a reference arm defining a first optical light path, the reference arm receiving the reference light and generating a reference light signal based on the reference light; a single sample arm defining a second optical light path and receiving the sampling light; an optical splitter arranged on the sample arm and configured to divide the sampling light into a plurality of sampling light beams; and an optical delay element configured to produce an optical delay between the plurality of sampling beams. The system is configured to simultaneously scan the plurality of sampling beams onto a surface of a sample. Also provided is a plurality of optical couplers each configured and arranged to receive and combine the reference light signal with one of a plurality of reflected light signals returned from a surface of the sample produced by each of the plurality of sampling beams to produce a plurality of interference signals, and a sensor configured to detect the plurality of interference signals. The interference signals include data representing digitized images of the sample.

In another embodiment, an optical coherence tomography system with space-division multiplexing includes: a light source producing light; a first optical device configured to split the light into reference light and sampling light; a second optical device configured to split the sampling light into a plurality of sampling beams; an optical delay element configured to produce an optical delay between the plurality of sampling beams; and a scanner configured to simultaneously scan the plurality of sampling beams onto a surface of a sample. The first optical device is further configured to generate an interference signal based on receiving reflected light signals returned from the surface of the sample produced by the plurality of sampling beams and the reference light. The interference signal includes data representing digitized images of the sample.

A method for imaging a sample using a space-division multiplexing optical coherence tomography system is provided. The method includes: providing an optical coherence tomography system comprising a light source producing light, a reference arm defining a first optical path, and a sample arm defining a second optical path; dividing the light from the light source into reference light and sampling light; transmitting the reference light to the reference arm to produce a reflected light signal; transmitting the sampling light to the sample arm; splitting the sampling light into a plurality of sampling beams on the sample arm; producing an optical delay between the plurality of sampling beams; scanning the plurality of beams onto a surface of a sample; collecting a plurality of reflected light signals each returned from the surface of the sample produced by each of the plurality of sampling beams; combining the plurality of reflected light signals into a single reflected light signal comprised of the plurality of reflected light signals; and combining the single reflected light signal and the reflected light signal to produce an interference signal, the interference signal comprising data representing digitized images of sample.

BRIEF DESCRIPTION OF THE DRAWINGS

The features of the preferred embodiments will be described with reference to the following drawings where like elements are labeled similarly, and in which:

FIG. 9 shows two-dimensional digital images of segments of the *Drosphila* larva captured during the in vivo imaging;

Figure 1:
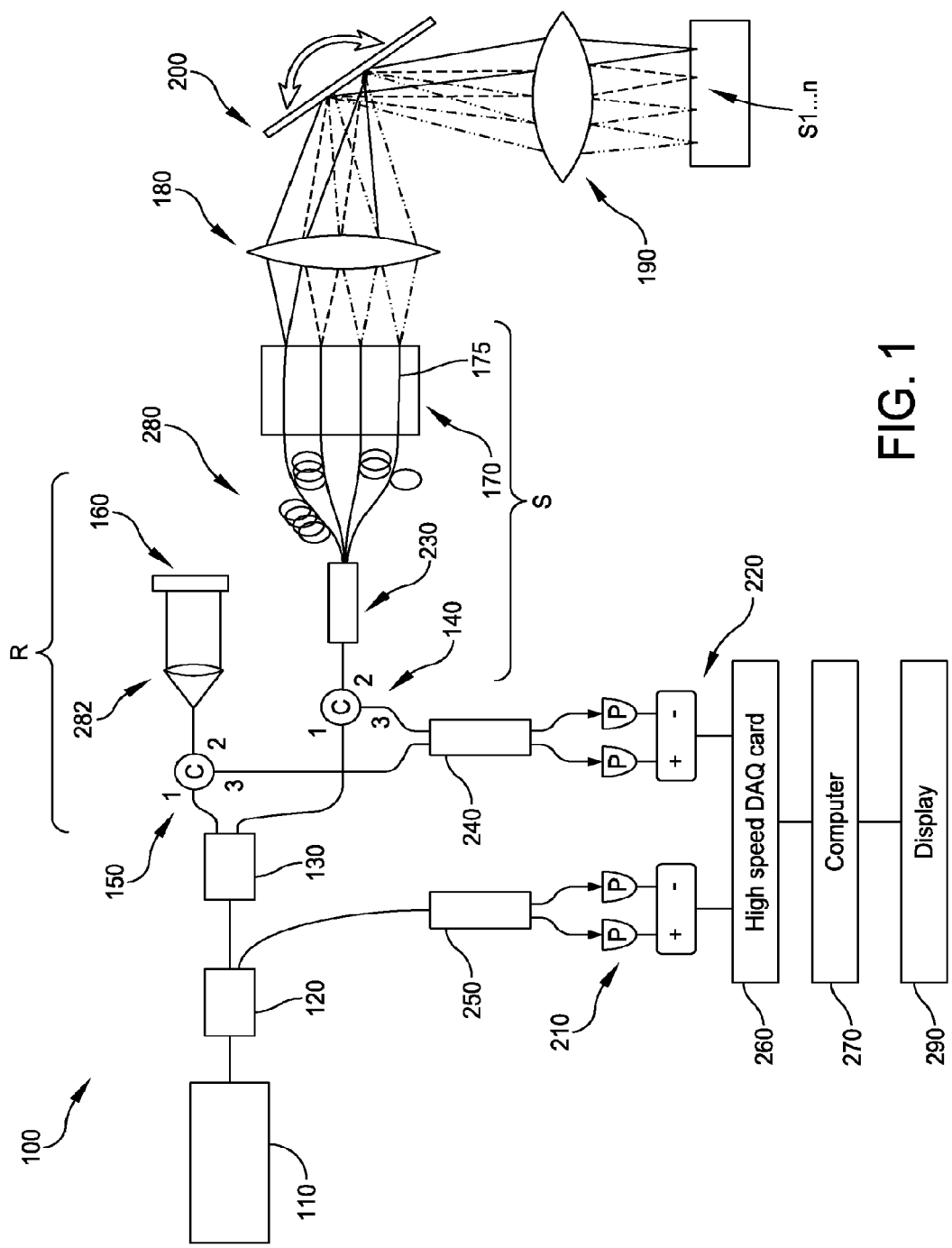
FIG. 1 is a schematic diagram of a space-division multiplexing optical coherence tomography (SDM-OCT) system according to one embodiment of the present disclosure.

All drawings are schematic and not to scale.

DETAILED DESCRIPTION OF THE INVENTION

The features and benefits of the invention are illustrated and described herein by reference to preferred embodiments. Accordingly, the invention expressly should not be limited to such preferred embodiments illustrating some possible non-limiting combination of features that may exist alone or in other combinations of features; the scope of the invention being defined by the claims appended hereto. This description of preferred embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. Accordingly, size, thicknesses, and spacing of various layers of materials or structures shown in the accompanying drawings are not limited to the relative sizes, thicknesses, or spacing shown in the accompanying drawings.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below,"

"up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms used herein to describe the physical relationship between various elements, features, or layers such as "attached," "affixed," "connected," "coupled," "interconnected," or similar should be broadly construed to refer to a relationship wherein such elements, features, or layers may be secured or attached to one another either directly or indirectly through intervening elements, features, or layers, as well as both movable or rigid attachments or relationships, unless expressly described otherwise. Similarly, the term "on" when used herein to describe the physical relationship between various elements, features, or layers should be broadly construed to include contact between one another that is direct or indirect through intervening elements, features, or layers, unless expressly described otherwise.

In one embodiment, an OCT system according to the present disclosure may utilize a wavelength tunable light such as a swept source laser OCT (SS-OCT) configuration as the basis for the light source and detection methodology. In SS-OCT, light from the source is divided into a sample arm (first optical path) and a reference arm (second optical path) of an interferometer arrangement. The light source is generally a coherent and broad wavelength tunable range light which is shined or scanned on an object or sample of interest. Scattered light reflected back from the object or sample by variations in the index of refraction within the sample is recoupled in the sample arm and then combined with the light that has traveled a fixed optical path length along the reference arm thereby generating an interference signal comprising an interferogram. The resulting interferogram is captured and measured through the detection arm of the interferometer by a sensor device. Fourier transformation is performed using a computer processor to analyze the optical frequency of the interferogram which relates to imaging depths of sampling light reflections returned from the sample. Reflections from different sampling depths produces interference patterns with different frequencies. Resolving the reflections via Fourier transformation processing produces a depth reflectivity profile (A-scan) of the sample. Scanning the sampling light beam in a first direction across the sample further produces two-dimensional (2D) images (B-scans). Scanning the sampling beam in a second direction allows creation of three-dimensional (3D) images of the sample.

The inventor has discovered that OCT imaging speed can be greatly improved with space-division multiplexing while maintaining imaging resolution and sensitivity. One unique feature of an optical coherence tomography (OCT) system according to the present disclosure is to split the imaging beam on the sample arm in order to illuminate multiple physical locations on the sample simultaneously. In some embodiments, a single sample arm may be used. Each beam is optically delayed by the system so that when images are formed, signals from different physical locations are detected in different frequency bands (i.e. imaging depth). Advantageously, this allows parallel detection of signals from multiple imaging points and therefore improves OCT imaging speed dramatically and preserves system resolution and sensitivity. Accordingly, embodiments of the present invention include space-division multiplexing OCT (SDM-OCT). A further advantage of a SDM-OCT system according to the present disclosure is that the system requires minimal modification to the current OCT system designs, while achieving significant improvement in system performance. A further benefit of the SDM-OCT system is that the system may utilize commercially available light sources.

FIG. 1 is a diagram showing a non-limiting exemplary embodiment of a SDM-OCT system 100 utilizing a wavelength tunable light source (e.g. swept-source or SS). The OCT system 100 may generally include a light source 110, a first optical device such as optical coupler 120, a second optical device such as optical coupler 130, a reference arm R defining a first optical light path (i.e. reference channel), a sample arm S defining a second optical light path (i.e. sampling channel), and other components as further described herein. The reference arm R provide an optical path of predetermine fixed length for generating a reference signal for comparison with reflected light signals returned from the object or sample under examination via the sample arm S, as further described herein.

In one embodiment, light source 110 may be a wavelength-tunable, long coherence light source to provide optimal imaging depth range. In one embodiment, without limitation, the coherence length may be greater than 5 mm to achieve proper imaging range for the SDM-OCT system. A commercially-available vertical-cavity surface-emitting laser (VCSEL) diode, such as for example without limitation Thorlabs Inc., SL1310V1 with a center wavelength of ~1310 nm, may be used as the light source for SDM-OCT system 100. Other suitable center wavelengths may be used. In one embodiment, the VCSEL laser may have a sweep rate of ~100 kHz, a tuning range of ~100 nm, and a coherence length of over 50 mm. The output of the laser from light source 110 may be ~37 mW. VCSEL diodes are essentially semiconductor-based devices that emit light perpendicular to the chip surface. It will be appreciated that other suitable light source specifications for VCSEL diodes and/or other types of light sources may be used. For example, a Fourier domain mode-lock (FDML) laser, or a MEMS tunable laser, such as from Axsun Technologies, Inc., Santec Corporation, Exalos Inc., or Insight Photonics Inc., etc. may be used.

The light beam output from the light source 110 is optically coupled to the first optical coupler 120 for dividing or splitting the single input light into two output light beams. An optical coupler (aka splitter) is generally a passive optical fiber device operable to couple and distribute light from one or more input fibers to one or more output fibers. Accordingly, optical energy input is split into multiple output signals retaining essentially the same properties as the input light. Suitable optical couplers include optical fiber couplers available from AC Photonics, Inc., Thorlabs, Inc. or other suppliers.

In one embodiment, without limitation, coupler 120 is configured to produce a 95/5 optical split, where 5% of the light is diverted to a Mach-Zehnder interferometer (MZI), while the remaining 95% of the light is used for the OCT imaging setup. MZIs are well known to those skilled in the art without further elaboration. The MZI signal acquired is used for phase calibration of the OCT signal in one embodiment. In other possible embodiments, the MZI signal may be omitted if an optical clock signal is used instead to clock the acquisition of the OCT signal (see, e.g. FIG. 4 without MZI). The invention is not limited to either arrangement. If an optical clock is used, it will be understood that the first optical coupler 120 may be omitted.

With respect to the optical couplers or splitters described herein (e.g. 120, 130, etc.), it will be appreciated that any suitable optical division or splitting of input light beams identified as a percentage of the incident beam (e.g. 5/95, 10/90, etc.) may be used depending on the intended application and system parameters. Accordingly, the invention is expressly not limited to those light division or split percentages disclosed herein which represent merely some of many possible designs that might be used for the couplers. It will be appreciated by those skilled in the art that the determination of the optical split ratio depends on how much light is intended to be directed into each of the sample and reference arms. It is desirable to have as much power as possible on sample while keep the power on sample to be within a safe limit. In the meantime, sufficient power is needed on the reference arm to get shot-noise limited sensitivity.

With continuing reference to FIG. 1, the sampling beam for the OCT imaging setup then is transmitted to the second optical coupler 130. In one embodiment, a 90/10 optical splitter may be used, where 10% of the input light is directed to the reference arm R (reference channel) and 90% of the light is directed to the sample arm S (detection channel). In the sample arm S, the input light beam goes through an optical circulator 140. In one embodiment, an optical circulator 140 is a three-port fiber optic device used to separate optical signals which travel in opposite direction in an optical fiber. Light which enters one of the ports (including reflected light traveling in an opposite direction than the incident light) exits the next port. In the present exemplary configuration, light for the sample arm S from coupler 130 enters port 1 of optical circulator 140 and exits port 2.

Figure 2:
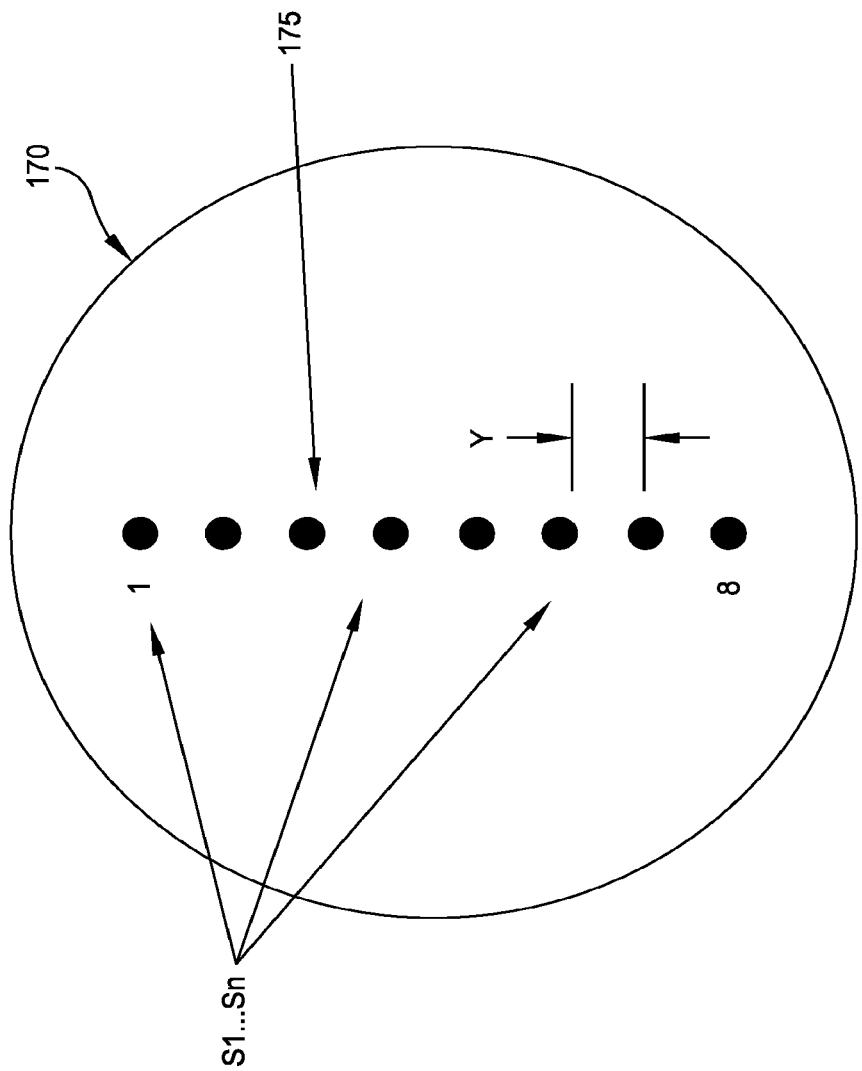
FIG. 2 is a transverse cross-sectional view of one embodiment of an optical fiber array.

The light sampling beam for sample arm S leaving port 2 of optical circulator 140 is then received and split by optical splitter 230. Splitter 230, which in one embodiment may be an optical fiber splitting device, may divide the sampling beam into at least two or more sampling beams at the output from the device. In one exemplary embodiment, without limitation, the sample arm light beam may be split by a 1×8 optical splitter and transmitted into eight different optical fibers 175 forming an optical fiber array 170 for sampling (see, e.g. FIG. 2). Each optical fiber 175 in the sampling fiber array 170 represents a sample location S1, S2, S3, ... Sn on the sample or specimen, where n=sample location number. In FIG. 1, it should be noted that only four of the eight optical fibers 175 are shown for simplicity and clarity.

In some embodiments, a planar lightwave circuit (PLC) splitter such as those available from PLC Connections, Inc. or others may be used. The optical splitter 230 functions to both transmit the optical signal via the fiber array 170 to the sample and to collect and combine the individual reflected sample return signals from the plurality of different sample locations, as further described herein. Advantageously, this configuration according to the present disclosure permits a single detection channel (sample arm S) to be used in lieu of multiple detection channels, which are at greater expense, complexity, and physical bulk for an OCT system equipment package.

Figure 12:
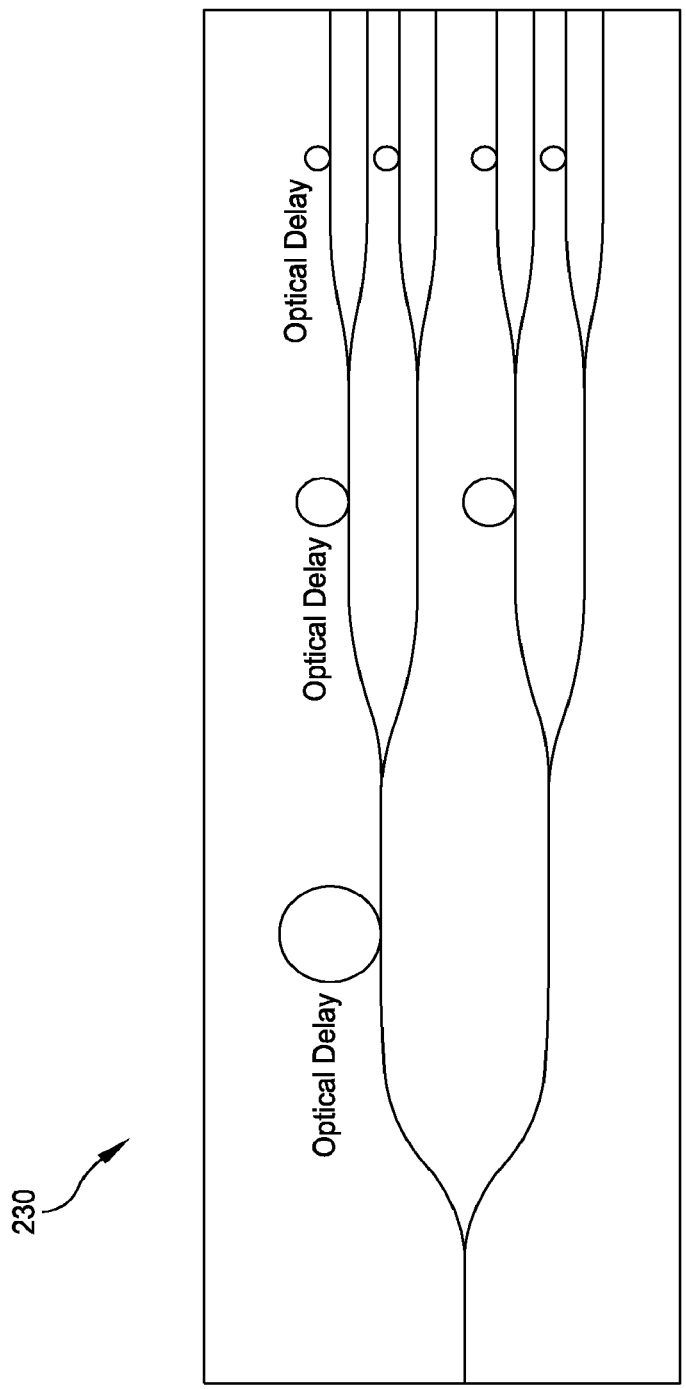
FIG. 12 is a schematic diagram of an optical delay element.

The above example uses an optical splitter, fiber optical delay and a fiber array to realize the optical splitting and delaying function. The same function can be realized in one embodiment with a custom planar lightwave circuit (PLC) splitter design as shown in FIG. 12. Here, the splitter 230 may be fabricated with the same amount optical power split into each channel and different optical delays built into the lightwave circuit. This device can be directly put on the sample arm S to illuminate the sample simultaneously with spatially separated beams.

It should be noted that an optical splitter 230 may be used that divides or splits the incident sampling light into more or less than eight output optical fibers 175 depending on the intended sampling application, number of sample locations desired, and other factors. Accordingly, the invention is not limited to any particular number of sampling optical fibers 175 in the sampling fiber array 170 or number of sampling locations (S1 ... Sn). Numerous variations and configurations are possible.

It should be noted that the optical light paths and optical coupling between components shown in the figures and described herein may be made by any suitable means including for example, without limitation, optical cables or fibers, relays, open-space transmission (e.g. air or other medium without physical contact between components), other light transmitting technologies presently available or to be developed, and any combination thereof. Accordingly, the invention is not limited to any particular optical coupling means and numerous variations are possible. In one embodiment, optical fibers may be used for optically coupling components together other than light transmission between lenses, mirrors, and/or the object or sample of interest.

With continuing reference to FIG. 1, OCT system 100 further includes an optical delay element 280 for producing a time delay in the sampling optical fibers 175. The combination of the optical splitter 230 and optical delay element 280 provides the space-division multiplexing aspect of the present embodiment of the invention. In one embodiment, without limitation, the optical delay element for producing the optical delay may comprise using multiple optical fibers 175 which each have different lengths (diagrammatically illustrated by the one or more coils or loops of each fiber in FIG. 1). The shorter optical fibers 175 will return a reflected optical signal from the sample to optical splitter 230 in less time than the longer fibers, thereby producing an optical time delay. Accordingly, in one embodiment, each fiber 175 may have a different length to produce an optical delay.

In one illustrative example, without limitation, the length difference between each optical fibers 175 may be about 2.5 mm. In one non-limiting example, for illustration, the length of the shortest and longest fibers in an exemplary fiber array may be about 50 mm and about 67 mm, respectively. Single mode fibers are used for OCT applications. It bears noting that the core of the optical fiber needs to be able to support single mode light transmission. For example, for 1310 nm, the fiber core diameter is ~9 um and for ~800 nm, it is about 6 um. The diameter of the fibers also depends on the index of refraction difference of the fibers. The cladding and outer diameter of the fiber can also vary.

It should be noted that other suitable fiber lengths and diameters may be used. Accordingly, numerous variations and configurations are possible.

In one embodiment, optical fibers 175 may be used which are formed a flexible and transparent fiber made of glass (ie. silica) or plastic and transmits light between each end of the fiber. In one example, the fibers 175 may be Corning Inc., SMF28 fibers.

The optical fibers 175 in fiber array 170 may be arranged in any suitable pattern. In one example shown in FIG. 2, without limitation, the optical fibers 175 may be arranged in a one-dimensional linear array with a suitable vertical spacing Y between fibers. A representative spacing Y of about 0.3 mm between fibers may be used in one non-limiting embodiment; however, smaller or larger spacing may alternatively be used in various embodiments. The vertical spacing Y between fibers may be uniform or different in the array. It should further be noted that patterns and arrangements of optical fibers 175 other than linear may also be used (see, e.g. FIG. 5 further described herein).

Figure 13:
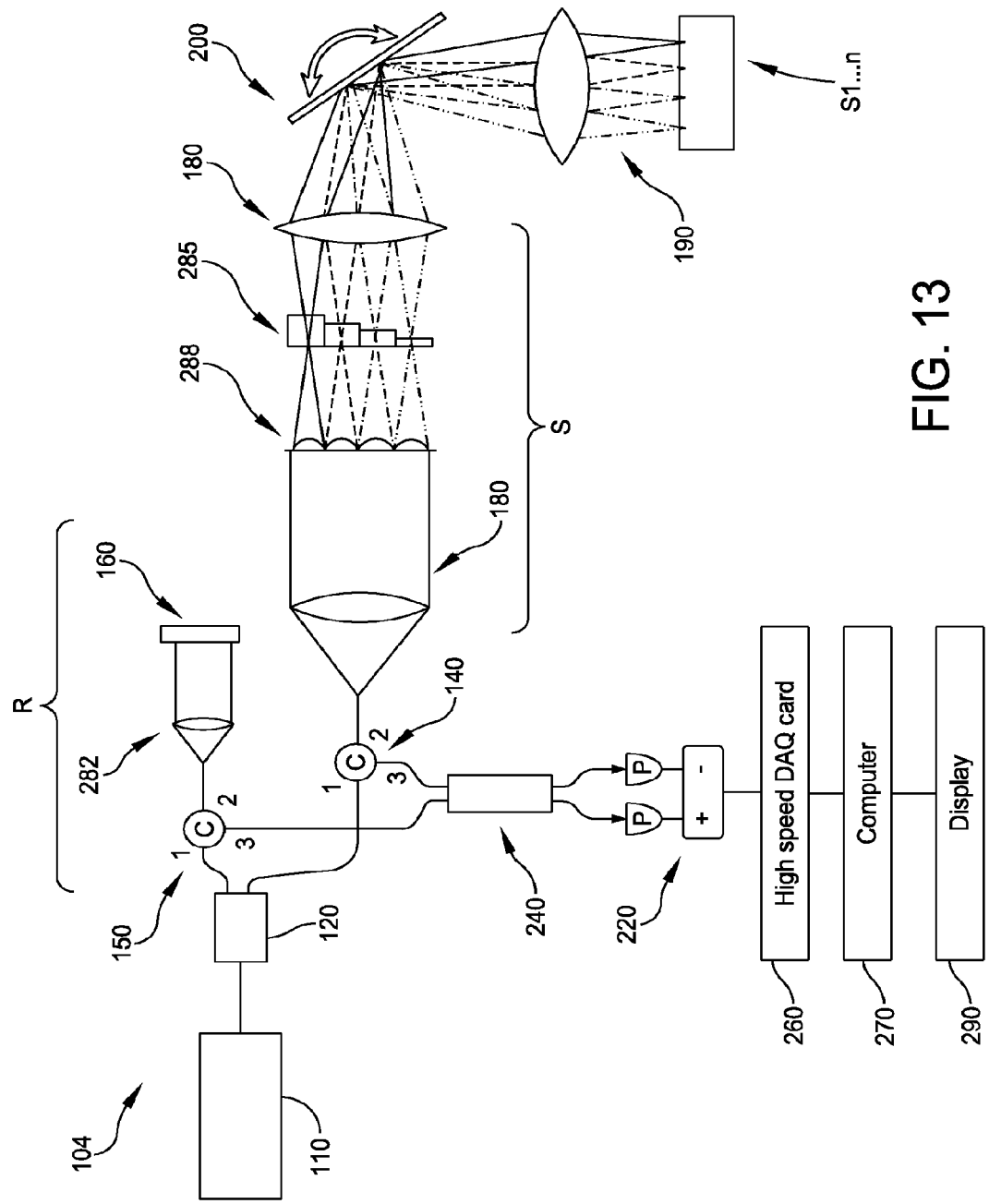
FIG. 13 is a schematic diagram of a third embodiment of space-division multiplexing optical coherence tomography (SDM-OCT) system.

It will be appreciated that other methods and devices may be used to produce the optical delay other than optical delay element 280 having different length optical fibers 175, which represents but one non-limiting exemplary embodiment. For example, an alternative optical delay element 285 is shown in FIG. 13 and further described herein. Numerous other variations and types of optical delay elements are possible which does not limit the invention.

With continuing reference to FIG. 1, sampling light from each of the different optical fibers 175 are transmitted through collimator 180 for focusing onto multiple different spots or sampling locations S1 . . . Sn on the sample. The sample can be scanned simultaneously by light from all optical fiber 175 using a scanning device such as without limitation a galvanometer scanner 200. The galvanometer scanner 200 may be a mirrored device which includes a galvo motor with an angled vibrating/oscillating (e.g. up and down) mirror driven by the motor shaft. Sampling light beams from each optical fiber 175 are independently transmitted and scanned across a surface of the sample by galvanometer scanner 200, thereby producing discrete and independent illuminated sampling spots or locations S1 . . . Sn each corresponding to one of the optical fibers. In one representative example, without limitation, each spot may have about 3 mW power on sample, and the light intensity fluctuation among all the spots may be less 1 dB. The galvanometer scanner 200 may project the sampling beams onto the sample in any suitable pattern to capture the desired image information. Other variations and types of scanning devices may be used. In some non-limiting examples, the galvanometer scanner 200 may be Cambridge Technologies, Model 6215H or Thorlabs, GVS102.

In one embodiment, the sampling beams transmitted by galvanometer scanner 200 may be focused onto the sample through a scanning objective lens 190. A 5× objective lens (e.g. Mitutoyo, 5×NIR or other) may be used in certain embodiments; however, other suitable lenses and powers may be used depending on the given OCT scanning application. It should be noted that the objective lens 190 does not need to be located right after the galvanometer scanner 200. Relay optics may also be inserted in the sample arm to focus the beam in some embodiments.

A plurality of back-reflected light signals emitted from the sample at the sampling locations S1 . . . Sn by each of the incident light sampling beams transmitted from the fiber array 170 travel in a reverse direction along the first optical light path and are reflected by the galvanometer scanner 200 through objective lens 190. The reflected light signals containing image information from the sample are collected by each optical fiber 175 of the fiber array 170 and relayed back to optical splitter 230 (reference FIG. 1). Each optical fiber 175 therefore is operable to transmit an individual sampling beam and receive back in return an individual respective reflected light or signal from the sample.

In one embodiment, the reflected light signals from the sample traveling back along the first optical light path in sample arm S may then be combined via the optical splitter 230 into a single reflected light signal (detection signal). This single reflected light/detection signal from the sample arm S is then combined with a reflected light reference signal returned from reference mirror 160 from the second optical light path (reference arm R) via optical circulator 150 by optical coupler 240 to create an interference signal, which is detected with a sensor such as in one non-limiting example a broadband balanced detector (photodetector) 220 (e.g. Thorlabs Inc., PDB480CAC, 1.6 GHz bandwidth). In one embodiment, without limitation, a 50/50 coupler 240 may be used which combines the reflected detection and reference signals in equal proportions or percentages. Other suitable percentages may be used. The balanced detector 220 operates to generate an interferogram from the interference signal. The MZI 250 optical path may also include a balanced detector 210 in some non-limiting embodiments wherein a MZI may be for phase calibration of the OCT signal, as described herein.

Interference signals from both the OCT system 100 and MZI 250 may be digitally acquired simultaneously using an appropriately configured high speed data acquisition (DAQ) card 260. In one illustrative embodiment, without limitation, high speed DAQ card 260 may be an Alazar Tech ATS9360 card operating at 1.2 GS/s or another suitably configured DAQ card. The acquired signal data from DAQ card 260 may then be streamed continuously to the memory of an appropriately configured computer 270 or memory accessible to another suitable processor-based device or PLC (programmable logic controller) through a suitably configured port. The signal data may be stored on the memory for further processing, display, export, etc.

The "computer" 270 as described herein is representative of any appropriate computer or server device with central processing unit (CPU), microprocessor, micro-controller, or computational data processing device or circuit configured for executing computer program instructions (e.g. code) and processing the acquired signal data from DAQ card 260. This may include, for example without limitation, desktop computers, personal computers, laptops, notebooks, tablets, and other processor-based devices having suitable processing power and speed. Computer 260 may include all the usual appurtenances associated with such a device, including without limitation the properly programmed processor, a memory device(s), a power supply, a video card, visual display device or screen (e.g. graphical user interface), firmware, software, user input devices (e.g., a keyboard, mouse, touch screen, etc.), wired and/or wireless output devices, wired and/or wireless communication devices (e.g. Ethernet, Wi-Fi, Bluetooth, etc.) for transmitting captured sampling images. Accordingly, the invention is not limited by any particular type of processor-based device.

The memory may be any suitable non-transitory computer readable medium such as, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

It will further be appreciated that various aspects of the present embodiment may be implemented in software, hardware, firmware, or combinations thereof. The computer programs described herein are not limited to any particular embodiment, and may be implemented in an operating system, application program, foreground or background process, driver, or any combination thereof, executing on a single computer or server processor or multiple computer or server processors With continuing reference to FIG. 1, still images and/or moving video images of the sample captured and recorded by the present OCT system 100 and the DAQ card 260 may be rendered on a suitable visual display 290 by computer 270 for observation by a system user. In healthcare related applications of the OCT system 100, in some possible embodiments, the user may be a health care provider, technician, or other professional. The sample images displayed on the visual display 290 are representative of the actual sample or specimen (e.g. human or other animal tissue in some embodiments) being analyzed by the OCT system 100 and useful as a diagnostic tool.

Figure 3:
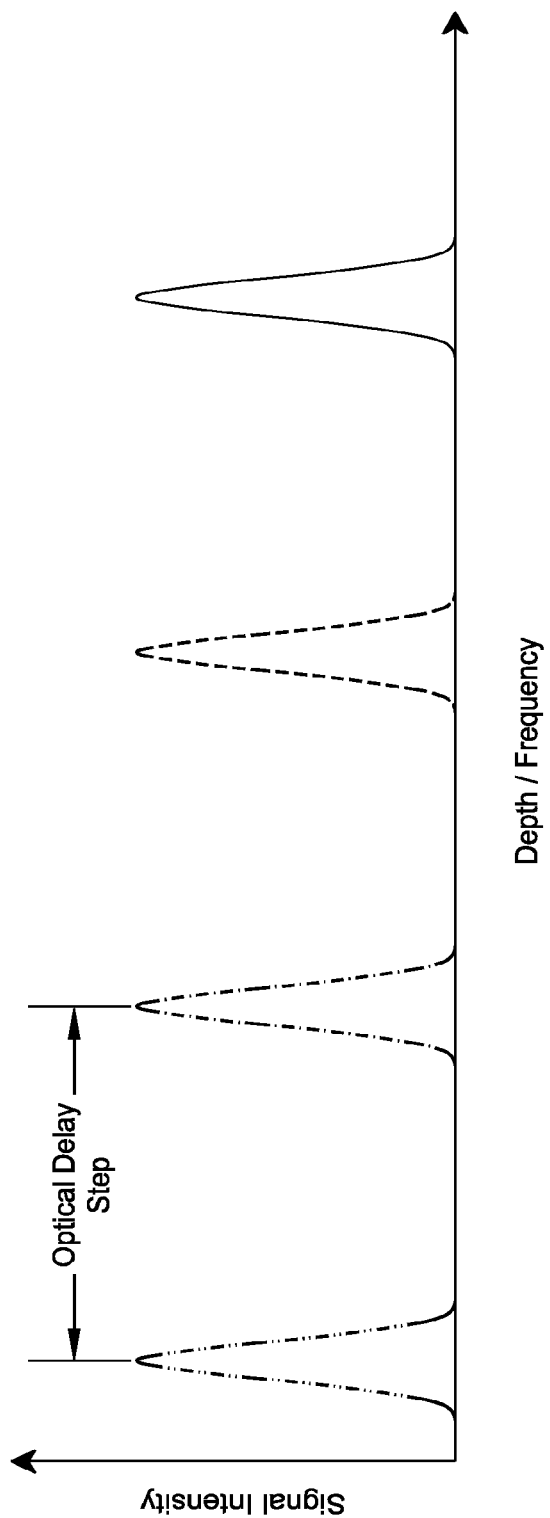
FIG. 3 is a graph illustrating an optical delay introduced into a plurality of light sampling beams according to the present disclosure.

FIG. 3 is a graph of signal intensity versus depth/frequency illustrating the optical delay of the OCT system 100. As shown, returned sampling beam signals detected from different spatial sample location S1 . . . Sn appear at different frequency bands/imaging depths in the final image. The amount of delay in frequency depends on the amount of optical delay introduced in the sample arm S.

Alternative Embodiment

Low Insertion Loss OCT System

Typically, when light is split from 1 fiber to N fibers using a splitter, the intensity for each of the output fiber is about 1/N of the input intensity. This allows even distribution of the light through all the output fibers. When reflected light is returned from the sample and passes through the splitter again, only about 1/N of the returned light is combined in the input fiber. This insertion loss is proportional to how many channels the splitter splits the light. In order to minimize the insertion loss for the returned beam, an alternative embodiment of an OCT system 102 is presented in FIG. 4.

Figure 4:
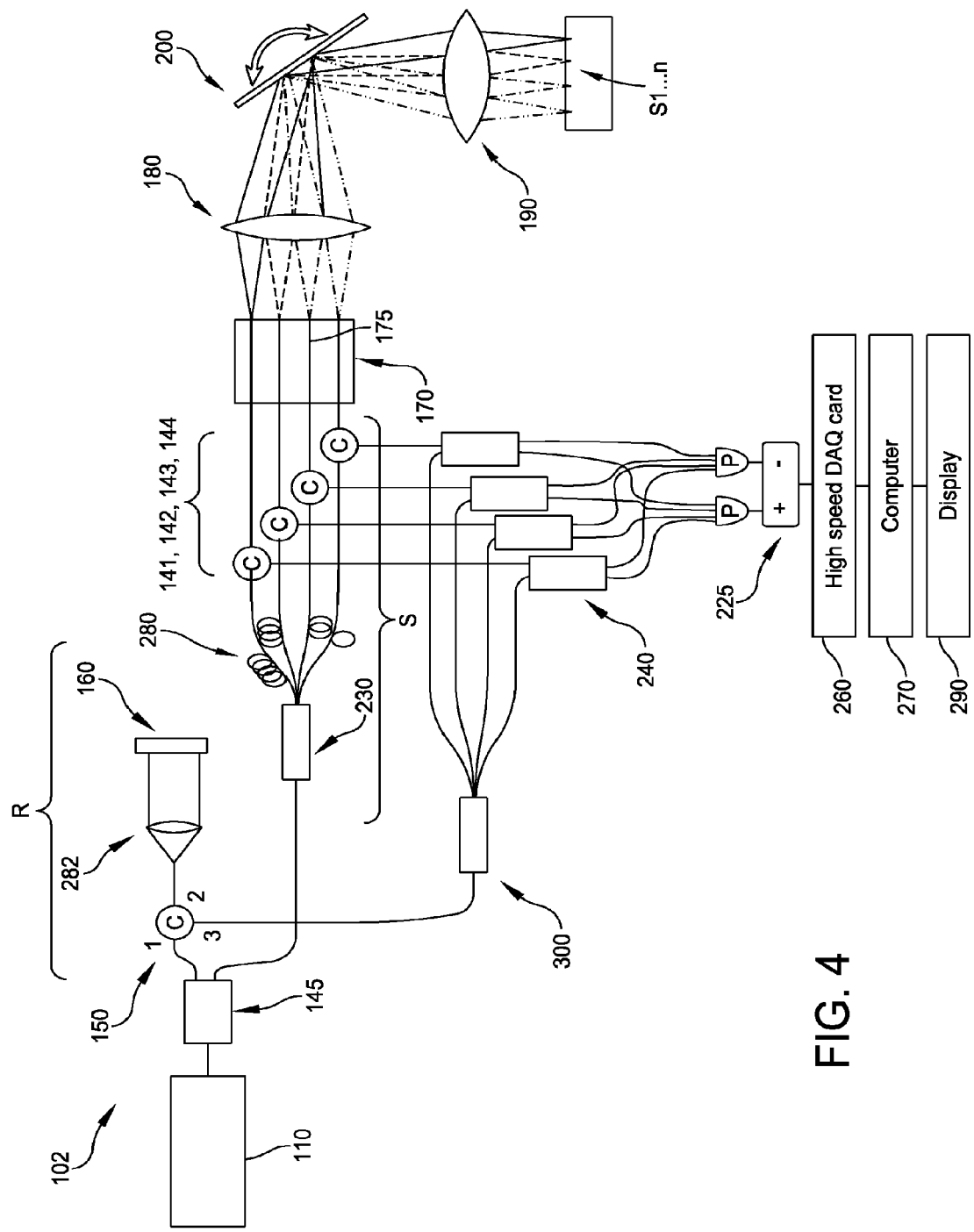
FIG. 4 is a schematic diagram of a second low insertion loss embodiment of space-division multiplexing optical coherence tomography (SDM-OCT) system.

Here, referring to FIG. 4, a low insertion loss OCT system 102 may include optical circulators 141, 142, 143, and 144 thereby providing an optical circulator for each of the optical fibers 175. In one embodiment, circulators 141-144 may be disposed in system 102 after (i.e. down path from) the optical splitter 230. The optical circulators 141-144 may be disposed after the optical delay element 280, and further in some embodiments before the collimator 180.

In this non-limiting example, four optical fibers 175 are shown to form the fiber array 170 for clarity of illustration, however, any suitable number of fibers may be used in the array. In some embodiments, without limitation, eight or more optical fibers 175 may be used as appropriate.

Returned (reflected) light collected by the scanner 200 from the sample will travel back through the circulators 141-144 in a manner already described herein, instead of and bypassing the splitter 230. The returned light from circulators 141-144 is transmitted to and will interfere with reference light from the reference arm R in four optical couplers 240 (which in one non-limiting embodiment may be 50/50 couplers). Each fiber 175 and circulator 141-144 may therefore have an associated coupler 240 in one non-limiting embodiment as shown; however, other variations are possible. The optical couplers 240 each combine the reference light with reflected light from one of the plurality of optical fibers 175 receiving reflected light from the sample to produce an interference signal.

A plurality of outputs signals each transmitted from one of the couplers 240 may then be combined and detected by a sensor such as a balanced detector (photodetector) 225. In one embodiment, a single balanced detector 225 may be provided. The insertion loss for the returned reflected light is then minimized using this approach, resulting in higher detection sensitivity. The optical circulators 141-144 can also be replaced in other embodiments by optical splitters instead to reduce cost, but at the expense of optical loss associated with splitters. However, either circulators or splitters may be used.

In the OCT system 102 of FIG. 4, it should further be noted that a single optical coupler 145 may be used downfield of the light source 110. In this embodiment, the coupler 145 may divert 80 percent of the light to the sampling arm S (detection channel) and 20 percent of the light to the reference arm R (reference channel). Other suitable beam splitting arrangements may be used. Light for the reference arm R is transmitted to optical circulator 150 from splitter 145 (entering port 1 and leaving port 2), collimator 282, and finally reference mirror 160 in a similar manner to OCT system 100 (see FIG. 1). The reflected reference light from mirror 160 travels back through circulator 150 and is output (from port 3) to a reference optical splitter 300. Optical splitter 300 then splits the single reflected reference light beam into four reference beams (reference channels) output to optical fibers in a functionally similar manner to splitter 230. These optical fibers are coupled to and provide the reference signals to each of the four optical couplers 240 to interfere with light from the sample arm S circulators 141-144, in the manner already described above. In one embodiment, without limitation, splitter 300 may be a planar lightwave circuit (PLC) splitter. Other suitable splitter, however, may be used.

Other components in FIG. 4 may be structurally and functionally similar to these same components which appear in FIG. 1, and have been described elsewhere herein.

Alternative Embodiment

Doppler OCT System

Figure 5:
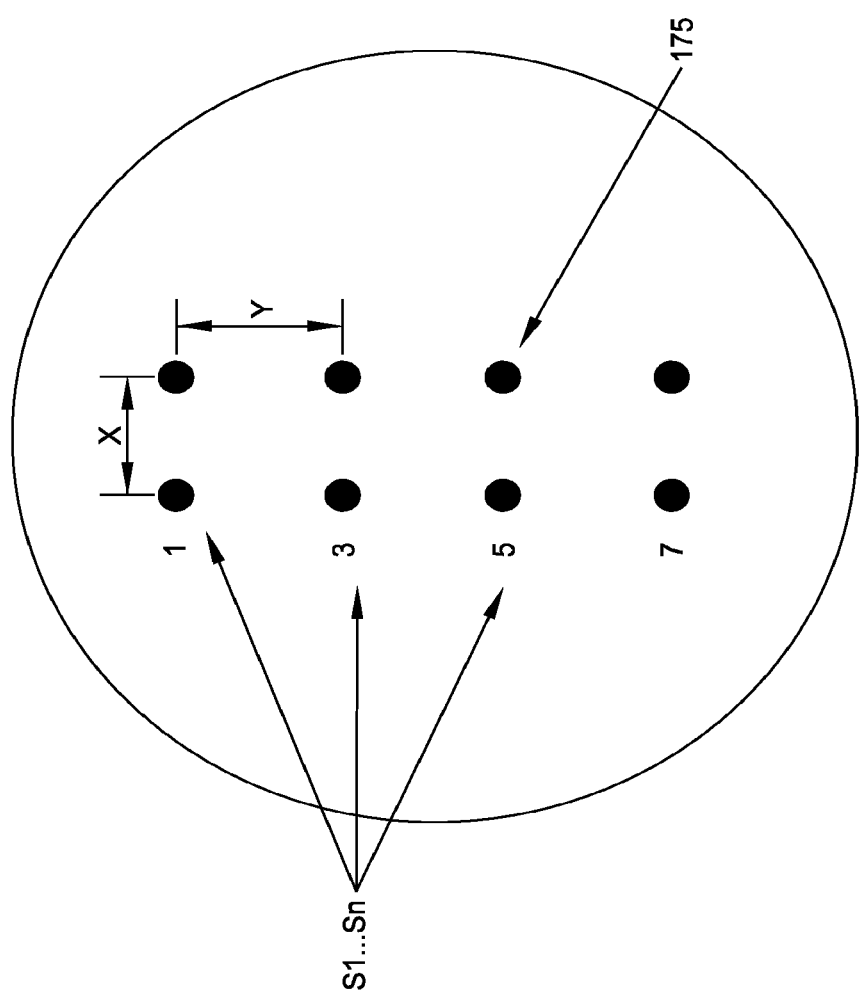
FIG. 5 is a transverse cross-sectional view of a second embodiment of an optical fiber array suitable for Doppler imaging.

FIG. 5 shows an alternative array design for the fiber array for a Doppler OCT system. In this case, the fibers may be arranged in an N×N array where N=the number of fiber in columns and rows. In one exemplary embodiment in a 2×N array, N=number of fiber rows. Images captured from the two pairs of fibers in each row will overlap during each B-scan. Phase differences from the overlapping image regions can be used to obtain Doppler flow information for the samples been imaged. The spacing between the two fibers in the same horizontal row can be adjusted to create different time delays between the two overlapping images, which determine the minimum flow speed that can be measured with the Doppler system using Doppler shift principles well known in the art. A longer delay corresponds to a slower flow speed, and vice-versa. Maximum flow speed may be determined by the time between consecutive A-scans. By choosing proper parameters for the A-line rate and time delay, for example in a health care application of an OCT system, blood flow speed within a large range can be measured. Simultaneous imaging from multiple imaging spots will also effectively improve the imaging speed for Doppler OCT. Any suitable horizontal spacing X in a row between two fibers and vertical spacing Y in a column between fibers may be used. The horizontal and vertical spacing X, Y may be the same or different, and the vertical spacing Y between rows of fibers may be different or the same. In one representative, but non-limiting example, the horizontal and vertical spacing may be 0.3 mm and 0.5 mm respectively.

The number of columns and rows in the N×N fiber array may be varied as needed. For Doppler OCT, one can use phase difference between A-scans from the same beam, A-scans between different source pairs in the same row, or A-scans between beams from different rows, each with its own Doppler sensitivity range. The combination of all these will provide a large dynamic range for Doppler measurements.

Figure 17:
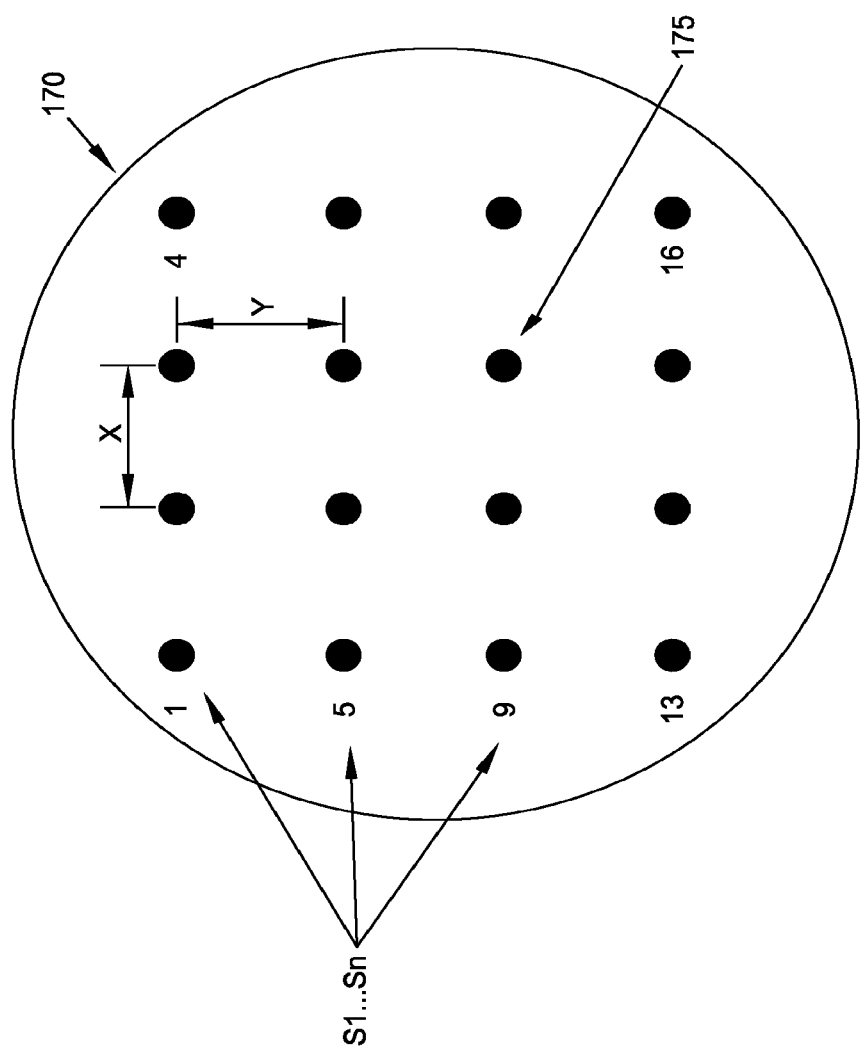
FIG. 17 is a transverse cross-sectional view of a third embodiment of an optical fiber array suitable for Doppler imaging.

FIG. 17 shows an alternative fiber array design. In this case, the fibers may be arranged in a 4×4 array. When used for structural imaging, the imaging speed will be improved by a factor of $N^2$. For Doppler OCT applications, phase difference measured between the same beam (e.g. between 1 and 1, between 2 and 2, etc.), or measured between different beams (e.g. between 1 and 2, 1 and 3, 1 and 4, etc.) from the same location of the sample can be used to obtain Doppler information with greatly improved dynamic range.

Doppler OCT may be used to generate angiogram and quantitatively measure blood flow information of the image sample. Doppler OCT is based on the Doppler effects, where scattering particles (e.g. red blood cells) moving towards or away from the light source generate Doppler phase shifts that are proportional to the flow speed that is projected along the direction of the light illumination.

It should be noted that the optical fiber 175 length difference between each sampling light beam does not need to be the same or uniform. In many situations, the sample or specimen surface is not flat (e.g. human retina, anterior segment of the eye, tooth, blood vessels, etc.). The fiber length difference can be arranged according to each specific application to allow maximum flexibility of the system design and best use of the imaging range.

The fiber array 170 may be used in most of the applications, although it is not necessary to put all the fibers in a single array. Fibers 175 may be used in different arrays or use individual fibers to image different samples or different locations of the sample simultaneously.

Another advantage of an OCT system according to the present disclosure is to make truly synchronized measurements from different illumination locations. This is helpful if a user wants to study the dynamic relationship of different locations on a single sample, or synchronized behavior from different samples (e.g. heart dynamics, neuron activities, etc.).

It should be noted that a balanced detector may be used to achieve maximum sensitivity for swept-source OCT, although a single detector or non-balanced detector can also be used. Accordingly, the present invention is not limited to the use of balanced detectors alone.

Although the method described here is based on swept-source OCT, the same approach can be used for spectral-domain OCT. In that case, the light source will be replaced with the broadband light source, with long-coherence length at each individual wavelength. The detector may be replaced with a spectrometer, comprising a collimating lens, a grating, a focusing lens and a digital line-scan camera or a 2D camera with high pixel count. All other components in the system may remain the same.

OCT Experimental Test

Figure 6:
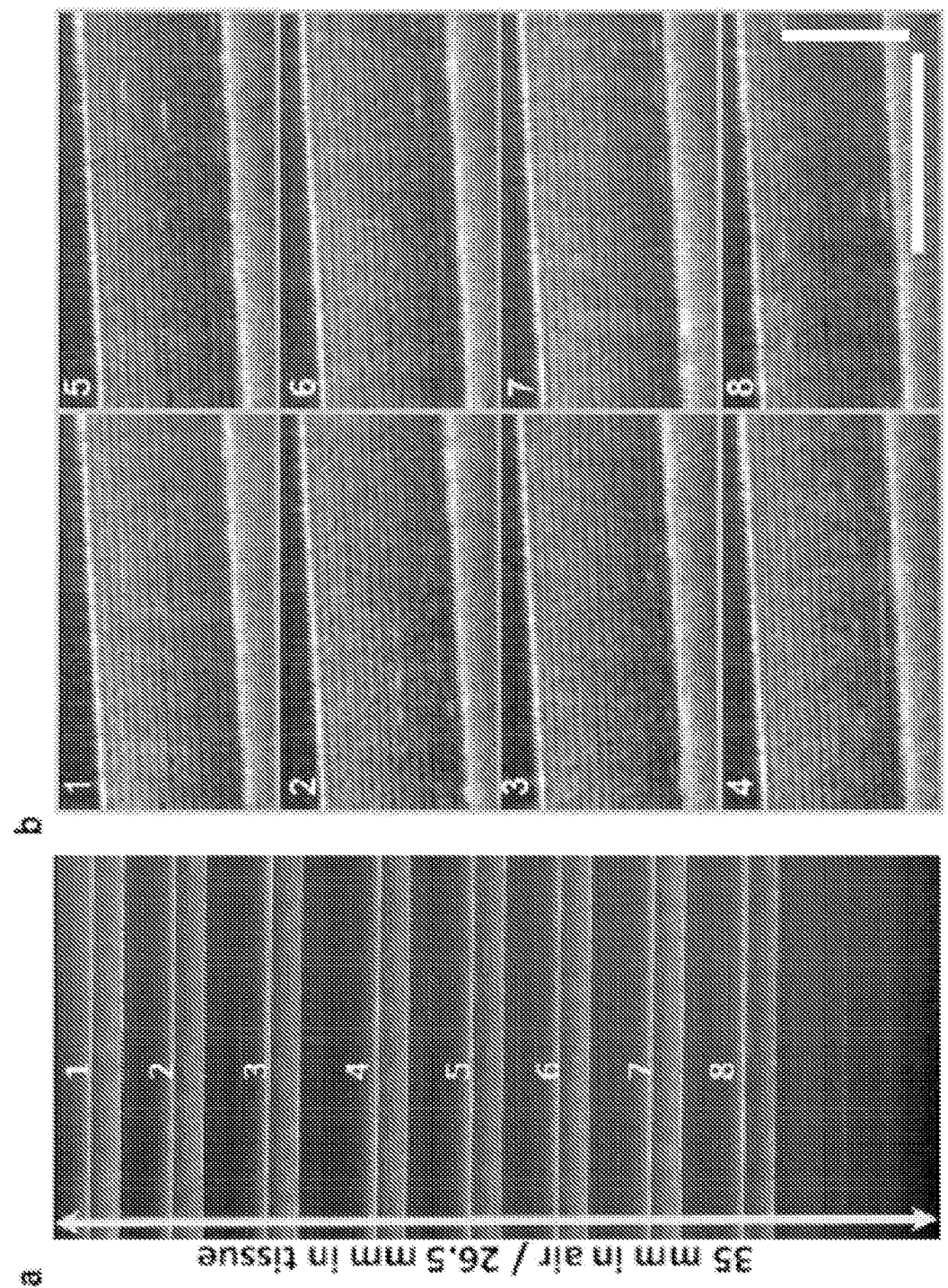
FIG. 6 shows actual digital images of a sample obtained with the SDM-OCT system of FIG. 1.

The performance of a space-division multiplexing swept-source OCT system according to the present disclosure was tested and validated on a static specimen or sample. FIG. 6 shows actual images obtained from an imaging test using a prototype system constructed according to the OCT system 100 of FIG. 1. The sample imaged in the test was a roll of Scotch® tape, where different layers (e.g. at different depths) of the tape can be clearly seen from the images obtained at different spots on the roll of tape. In this application, eight (8) optical fibers 175 each producing a sampling beam were used in the sampling arm S of the test setup, thereby obtaining discrete images at eight different locations in the tape roll sample from the beams labeled 1 to 8. The light source and other appurtenances used for the test were as described herein for OCT system 100 and shown in FIG. 1.

The entire imaging range (e.g. depth) of the OCT system 100 was about 26.5 mm in tissue (35 mm in air) in this test (see Image "a" at left in FIG. 6). Scotch® tape images from the roll seen at different depths correspond to images obtained from the eight different imaging locations. Zoomed-in images of each of the eight sample locations S1 . . . S8 in the tape roll are shown on the right in FIG. 6, demonstrating relatively uniform image intensity from the different sampling beams. Even at the deepest imaging depth (S8), individual layers of the tape as shown at right can still be clearly identified. This suggests that axial image resolution is preserved across the entire imaging range of depths. Furthermore, the imaging results using a calibrated reflecting mirror in the sample arm show that an axial resolution of ~8.3 um in tissue and an over 95 dB sensitivity can be obtained using the prototype OCT imaging system. Since the VCSEL laser is operated at ~100 kHz (light source 110), simultaneous imaging with the 1×8 fiber array 170 achieves an ~800 kHz effective A-scan rate combining all eight beams. It should be noted that the results were obtained using a single detection channel albeit with eight sampling beams.

Although the present prototype OCT system 100 demonstrates a factor of 8 in improvement of imaging speed, further improvement of imaging speed can be achieved by using a fiber array with more fibers. The ultimate limit for the imaging speed is no longer the sweep-rate of the light source. Instead, the imaging speed can be scaled up with the improvement of the coherence length of the light source, the bandwidth of the detector, the speed of the data acquisition, the number of fiber channels, and the optical path length difference between each fiber.

In Vivo OCT Experimental Test

In Vivo OCT System Setup

An in vivo test of the OCT system 100 of FIG. 1 was performed to the capture of moving images of the beating heart of a *Drosophila* (fruit fly) larva. A commercial VCSEL tunable laser 110 (SL1310V1, Thorlabs Inc.) with a center wavelength of 1310 nm was used for the OCT system. The laser had a swept rate of ~100,000 Hz, a tuning range of ~100 nm, and a coherence length of over 50 mm. The output power was ~37 mW. A 95/5 optical coupler 120 (AC Photonics, Inc.) was connected to the laser output and 5% of the light was directed to a Mach-Zender interferometer (MZI), which has an optical path length difference of ~60 mm in air for the two arms R (reference) and S (sample). The remaining 95% of the light was used for OCT imaging.

Figure 7:
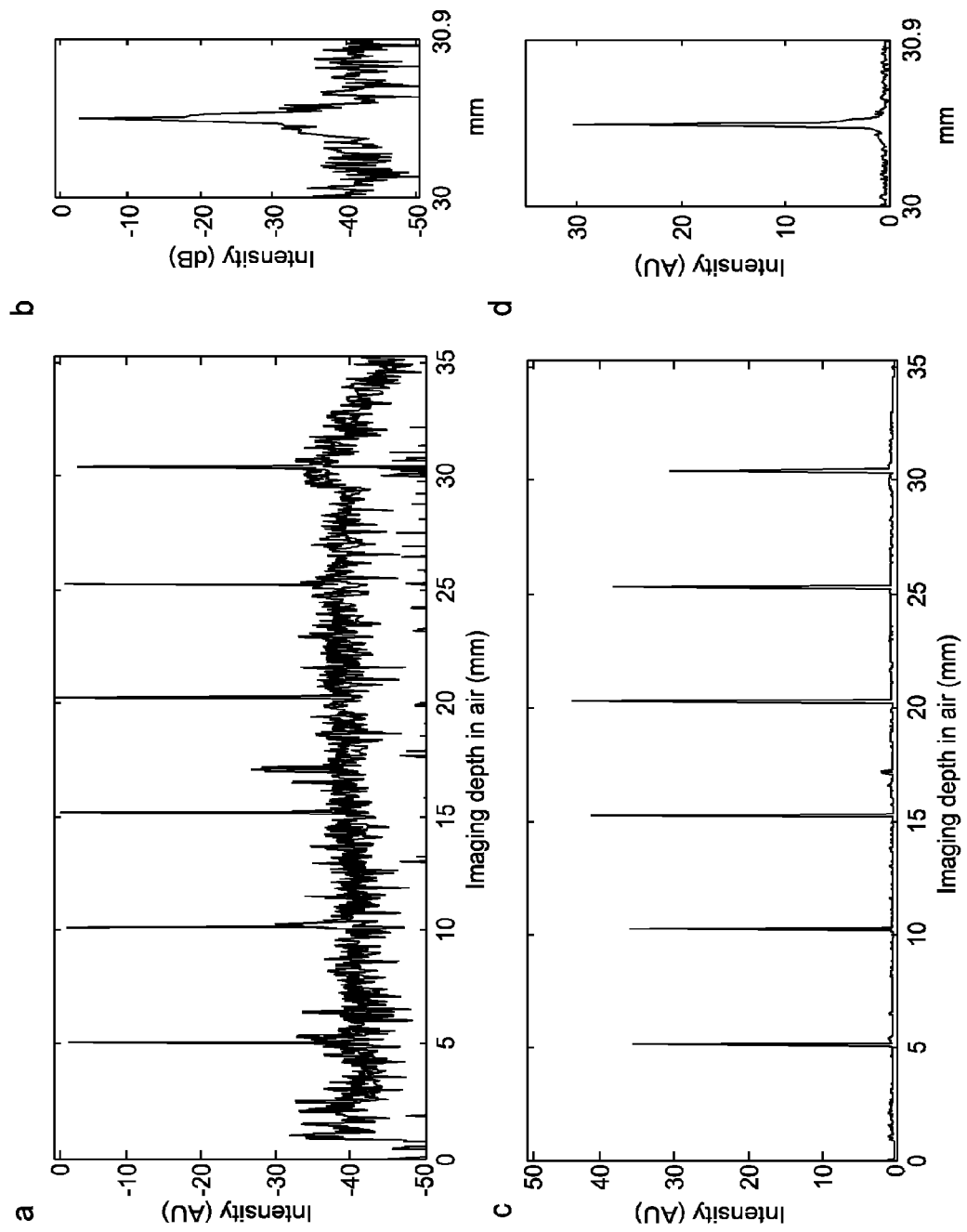
FIG. 7 are graphs showing measured sampling point-spread-function from different scanning depths of a sample.

A 90/10 optical coupler 130 provided 10% of the light to the reference arm R and 90% of the light to the sample arm S. Input light to the sample arm S was split into 8 fibers using a planar lightwave circuit (PLC) splitter 230 (e.g. PLC Connections, Inc. or similar). Output optical fibers 175 from the PLC splitter were custom arranged in a one-dimensional (1D) array (1×8, FIG. 2), with a length different of ~2.5 mm between each fiber. Spacing was about ~300 um between each fiber in the 1D array and about ~370 um after the spots were projected on samples. The surface of the fiber array 170 was angle polished at ~8 degrees to minimize light reflection. Light from different fibers were focused onto different spots on the sample, which were synchronously scanned by a pair of galvanometers (Cambridge Technology, Inc.). Each spot had about 2 mW power on sample. Light intensity variation among all the spots was less than 1 dB. Optical circulators (AC Photonics, Inc.) were utilized on both the sample and reference arms S, R to route reflected signal from both arms to interfere at a 50/50 coupler 240. Broadband balanced detectors 210, 220 (1.6 GHz, PDB480CAC, Thorlabs Inc.) were used to detect interference signals from both the OCT system and the MZI. Outputs of the balanced detectors were digitally acquired simultaneously using a high speed data acquisition card 260 (ATS9360, Alazar Tech) at 1.2 GS/s. Data from both channels (8320 points for each channel per sweep) was streamed to the computer 270 memory continuously through the PCIe port. The entire imaging range of the prototype system was about 35 mm in air (or 26.5 mm in tissue). A 5× objective lens 190 (Mitutoyo, 5×NIR) was utilized to provide about 11 um transverse resolutions. The axial resolution was measured to be about 11 um in air (or about 8.3 um in tissue) throughout the depth range (see FIG. 7, measured point-spread-function from different depths). A 94.6 dB sensitivity was measured using a calibrated reflector (−43.4 dB) and a roll-off of <2 dB was observed at ~30 mm depth. Since the VCSEL laser was operated at ~100,000 Hz, simultaneous imaging with all 8 fibers achieved an effective axial scan rate of ~800,000 A-Scans/s.

*Drosophila* Larvae Preparation

*Drosophila* is a widely used model system for developmental biology due to the ease in culturing and its short lifecycles. In vivo OCT images in FIG. 8 were obtained from a third instar *Drosophila* larva. At this stage, the heart tube is located at the dorsal midline, spanning segments T2 (anterior end) to A8 (posterior end), being attached to its dorsal epidermis by seven pairs of alary muscles. The larva was mounted onto a black clip board using a double-sided tape with its dorsal side facing upwards.

In Vivo Imaging and Signal Processing

To obtain 3D imaging of the *Drosophila* larva, 400×80 A-scans covering ~1.1 mm×0.4 mm was acquired in ~0.37 seconds (s). The MZI signal acquired simultaneously with the OCT signal was utilized for phase calibration for each laser sweep. Eight images from the 8 beams were segmented from different depth ranges and digitally combined to form a volumetric dataset consisting of 400×605 A-scans covering the entire larva (~1.1 mm×3.0 mm range). To obtain M-mode imaging from the larva heart, 400 B-scans with each containing 400 A-scans over ~250 um range around the heart tube were acquired for about 2 seconds. The frame rate for the B-scan was ~217 frames per second. Images from different heart segments were digitally combined. Functional information of the heart was analyzed following established methods. Matlab (Mathwork, Inc.) was used to process the data, and ImageJ (NIH) and Amira (VSG, Inc.) were used to generate videos and render images for presentation.

In Vivo Test Results

Figure 8:
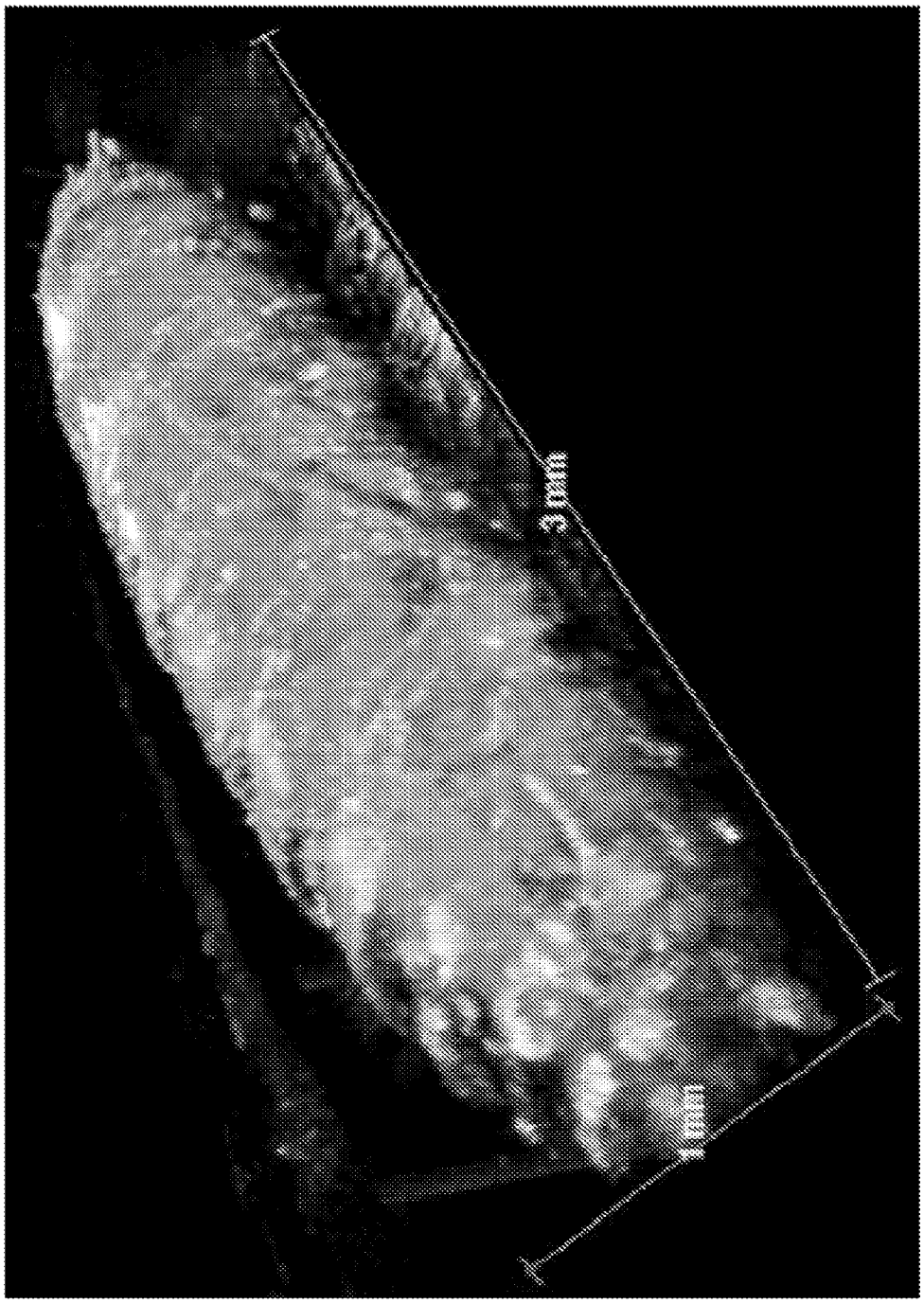
FIG. 8 is a three-dimensional digital image of a *Drosophila* larva captured during in vivo imaging using the SDM-OCT system of FIG. 1.

Results of the in vivo 3D SDM-OCT imaging of a *Drosophila* larva is demonstrated in FIGS. 8-11. The entire 3D dataset (400×605 A-scans, FIG. 8 showing entire larva in a merged 3D image), assembled using images from all 8 beams, was obtained in less than 0.37 seconds. The actual size of the larva was ~1 mm wide by ~3 mm long. FIG. 9 shows cross-sectional and en-face images of the larva. The heart tube (H) and the trachea structures (T) are clearly observed.

Figure 10:
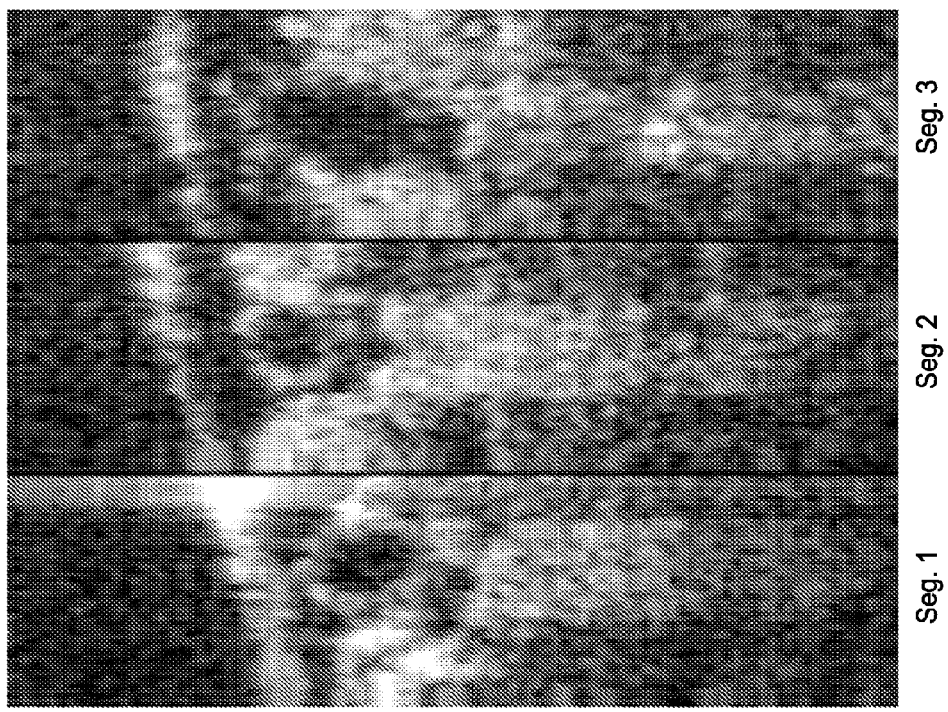
FIG. 10 shows simultaneous two-dimensional digital images of segments of the *Drosphila* larva captured during the in vivo imaging which reveal the beating heart tube of the insect.
Figure 11:
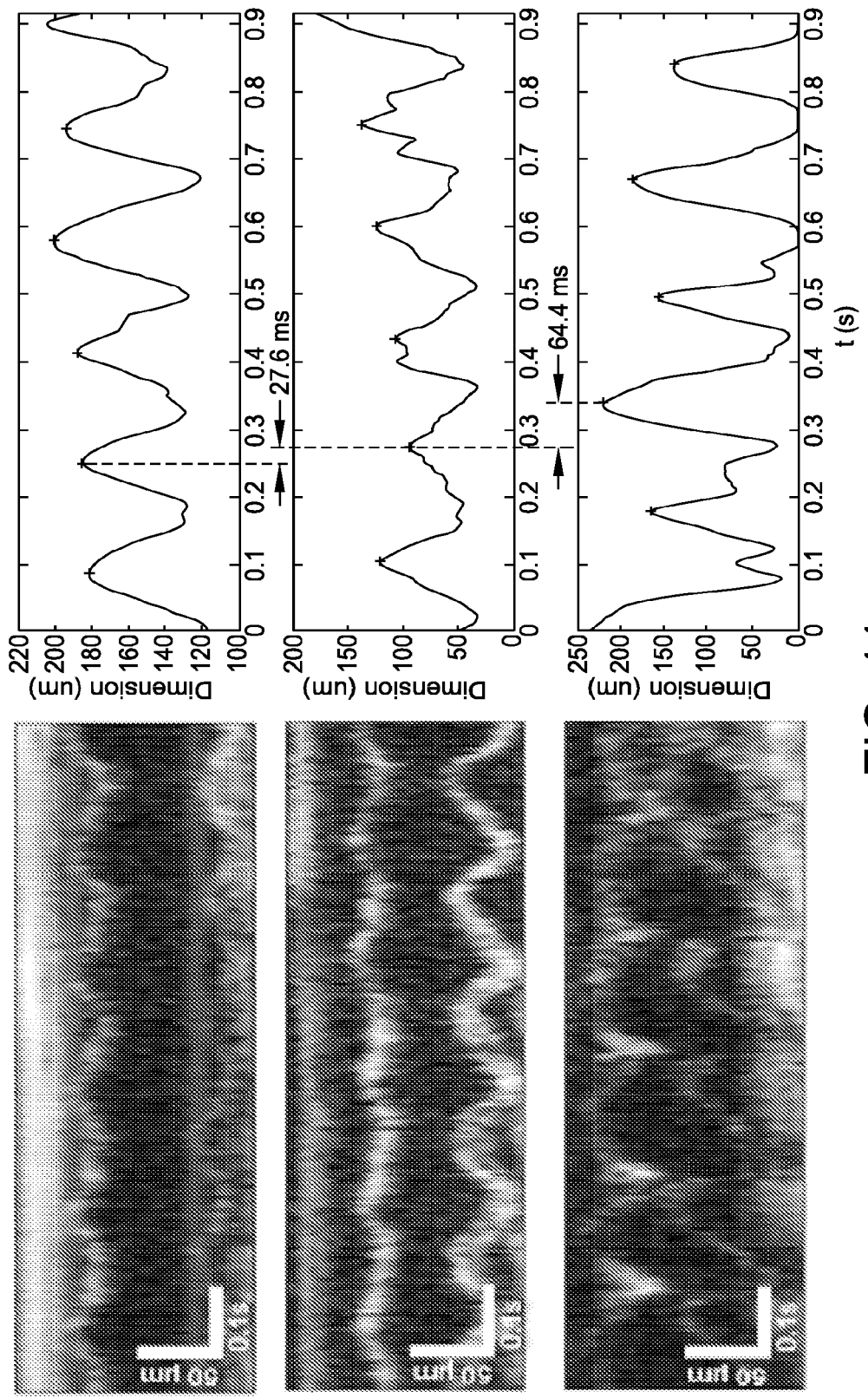
FIG. 11 shows digital images of segments of the *Drosphila* larva captured during the in vivo imaging which reveal the beating heart tube of the insect captured by M-mode imaging.

To demonstrate synchronized imaging capability, M-mode B-scan imaging was performed over three segments of another larva heart, roughly corresponding to the A7, A6, and A5 segments. A frame rate of ~217 frames per second was obtained at all segments simultaneously. Representative cross-sectional synchronized still images showing all three segments of the beating heart tube is shown in FIG. 10. A video demonstrating the synchronized beating of the heart tube segments was obtained, from which the still images have been extracted. Segment 1 beats first, Segment 2 follows, and Segment 3 then follows Segment 2.

The functions of the larva heart were further quantified by the in vivo testing. In addition to functional information, such as heart rate (372 beats per minute), end systolic (36 μm for A7, 32 μm for A6, and 11 μm for A5) and diastolic dimensions (60 μm for A7, 74 μm for A6, and 58 μm for A5) and fractional shortening (42% for A7, 56% for A6, and 80% for A5), also observed was a delay between the dilation and contraction in segment A6 compared to A7 (14 ms), and segment A5 compared to A6 (69 ms) shown in FIG. 11. This delay suggested the contraction of the heart tube was initialized in the A7 segment (posterior) and propagated toward the A5 segment (anterior). This finding is consistent with previous literature on *Drosophila* larvae heart development.

In summary, an 8× improvement in imaging speed was demonstrated by the experimental tests. Further speed improvement is straightforward. In fact, the effective A-scan rate is scalable to the number of spots shine on the sample simultaneously, while only a single detection channel is required. For optical coherence microscopy (OCM) applications, where the imaging penetration depth is limited to less than a few hundred microns, 16 channels or more can be used. Optical delay between each channel needs to be shortened accordingly in order to fit images from all channels into the detection range using current hardware.

Fundamentally, the spatial multiplexing technique would have resolution and sensitivity advantages compared to the approach of increasing laser sweep rate. Since the laser sweep range was preserved, axial resolution for OCT was not compromised as the effective A-scan rate was increased. Meanwhile, the dwell time at each imaging spot was maintained at a relatively low laser sweep rate. More data sampling points were also recorded within the dwell time for the SDM-OCT system 100. Imaging speed improvement was achieved by performing parallel detection utilizing multiple sampling beams. This is in contrast to increasing the laser sweep rate, where the dwell time and the number of sampling point for each sweep is reduced. In OCT system 100, the PLC splitter has an about 10 dB insertion loss. This is not an issue in the forward direction, as the input light is evenly split into the 8 beams. However, when combining the reflected light from the sample, the 10 dB insertion loss resulted in reduction in sensitivity. As a result, about a 95 dB sensitivity was achieved over the entire imaging range when only about 2 mW light was shined on the sample for each spot. This is about 11 dB lower compared to shot-noise-limited sensitivity. However, alternative designs bypassing the PLC splitter in the return path (see, e.g. FIG. 4) or using low-loss optical combiners may be utilized to further improve imaging sensitivity.

With the space-division multiplexing technique, the bottleneck for further improving SS-OCT imaging speed is no longer the sweep rate of tunable lasers. Instead, high speed data acquisition and high throughput data transfer are greatly desired. The data acquisition card used in testing the prototype system according to the OCT system 100 of FIG. 1 supports a 12-bit 1.8 GS/s sampling rate. However, due to limited data throughput, data could only be acquired from both the OCT and MZI channels simultaneously at 1.2 GS/s. Further improvement in the speed of data acquisition and throughput, the bandwidth of the detectors, the coherence length of the light source, and the number of fiber channels will advantageously scale the OCT imaging speed linearly without significant changes in system design. Since the input light from source 110 is split into multiple beams, a powerful light source is desirable.

In conclusion, the testing successfully demonstrated a space-division multiplexing technique for OCT, which achieved significant improvement in imaging speed while preserved axial resolution. Although the space-division multiplexing technique was demonstrated based on SS-OCT, the same approach can be applied to SD-OCT. In that case, a broadband light source with long coherence length for each wavelength and a spectrometer, comprising a collimating lens, a diffraction grating, a focusing lens and a line-scan camera or a 2D camera with high pixel count, may be needed to provide deep imaging range.

FIG. 13 illustrates an additional embodiment of an OCT system 104 with an alternative optical delay element 285, which may also be used with the OCT system 100 of FIG. 1 or other embodiments. Here, a swept-source OCT detection method is used, although the design applies to spectral-domain OCT detection methods as well.

In this embodiment shown in FIG. 13, light on the sample arm S is collimated by collimator 150 and then shined onto a microlens array 288. A commercially available microlens array 288 may be used, such as for example without limitation Edmund Optics, Model #63-230. Each microlens of the array 288 will focus a portion of the sampling light beam onto a small spot at the intermediate image plane. The microlens array 288 splits/divides the single incident sampling light beam into a plurality of light beams, thereby obviating the need for an optical splitter such as splitter 230 in FIG. 1. In addition, it should be noted that the divided multiple sampling light beams output from microlens array 288 may not be captured and transmitted by optical fibers, but rather transmitted through space in a medium.

With continuing reference to FIG. 13, an optical delay element 285 comprising a plurality of adjoining optically transparent glass or plastic elements members each having a different thickness to create different optical delays for each sampling beam. The optical delay element 285 may be disposed at the intermediate image plane in one embodiment, or off the intermediate image plane in other embodiments as long as different beams do not overlap. Therefore, beams focused at different locations on the sample are optically encoded in different frequency bands in the final detected signal. The amount of delay in frequency depends on the amount of optical delay introduced in the sample arm S by glass or plastic members. Note that although the optical delay element 285 is placed at the intermediate imaging plane in this example, it can be placed at other locations in the sample arm S, for example, between the collimator 180 and the microlens array 288. Each of the sampling light beams from optical delay element 285 are transmitted to a relay lens 222, galvanometer scanner 200, and objective scan lens 190 onto the sample simultaneously at sample locations S1 . . . Sn.

Other components of OCT system 104 may be similar in function and design to the corresponding components labeled the same in FIG. 1. In one possible configuration of OCT system 104, without limitation, optical coupler 120 may be configured to divert 3% of the light from light source 110 to the reference arm R and 97% of the light to the sampling arm S. Other suitable splits are possible.

In yet other possible embodiments, optical delay element 285 may be used in the OCT system 100 of FIG. 1 in lieu of optical delay element 280. In that case, the light beams from each of the individual optical fibers 275 output from splitter 230 may be shined onto the optical delay element 285 in manner similar to that shown in FIG. 13.

Figure 14:
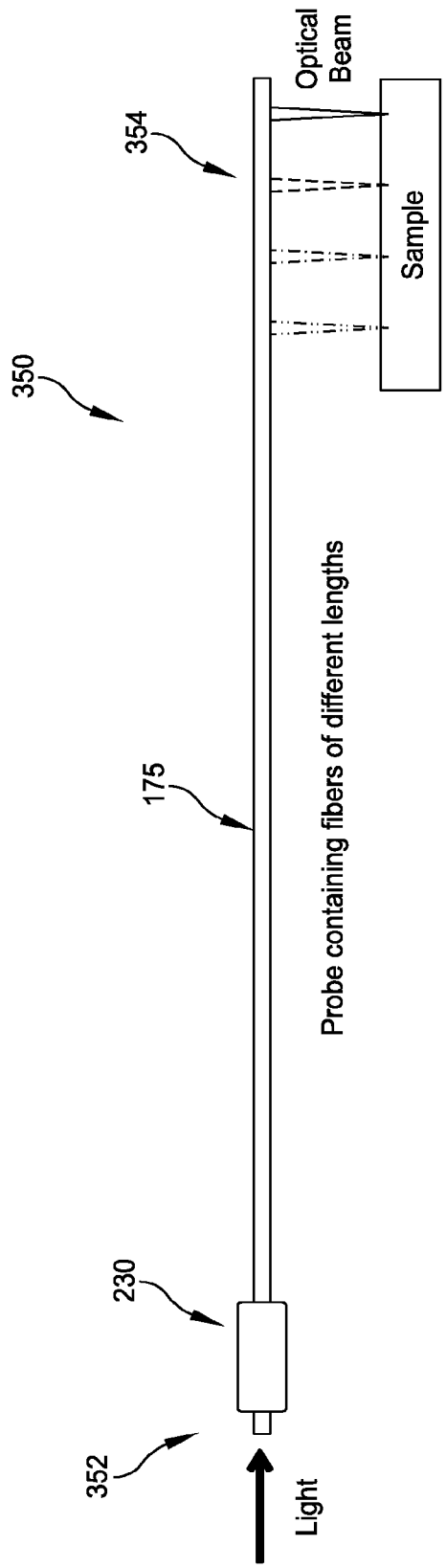
FIG. 14 is an illustration of an exemplary embodiment of an OCT probe.

FIG. 14 shows one possible embodiments of a probe based OCT system usable with the OCT system 100 of FIG. 1. The probe 350 can be used for various applications, such as for example without limitation cardiac vascular OCT as well as for endoscopic OCT. In one embodiment, the probe 350 may have a generally tubular body defining an interior passageway for routing the optical fibers 175 through the probe. An optical splitter 230 may be placed at the proximal end 352 of the probe 350 and splits the input light beam into several optical fibers 175. Each fiber 175 has a different length, and shines light through the side of the probe 350 at a distal end 354 such as through a microlens for focusing the optical sampling beams to acquire signals from different locations of the sample simultaneously. The sampling beams may be emitted at any suitable angle from the probe 350 with respect to the distal end 354 between 0 and 180 degrees. In one exemplary embodiment, the angle may be ~90 degrees. To scan the individual sampling beams linearly across the sample, the proximal end 352 of the probe 350 may be rotated by a suitable motor drive which will then rotate distal end 354 from which the sampling beams are emitted. Because the area to cover on the sample is generally large for cardiovascular and endoscopic OCT applications, high speed is desirable for these applications. The use of multiple sampling or scanning beams efficiently solves this problem.

Figure 15:
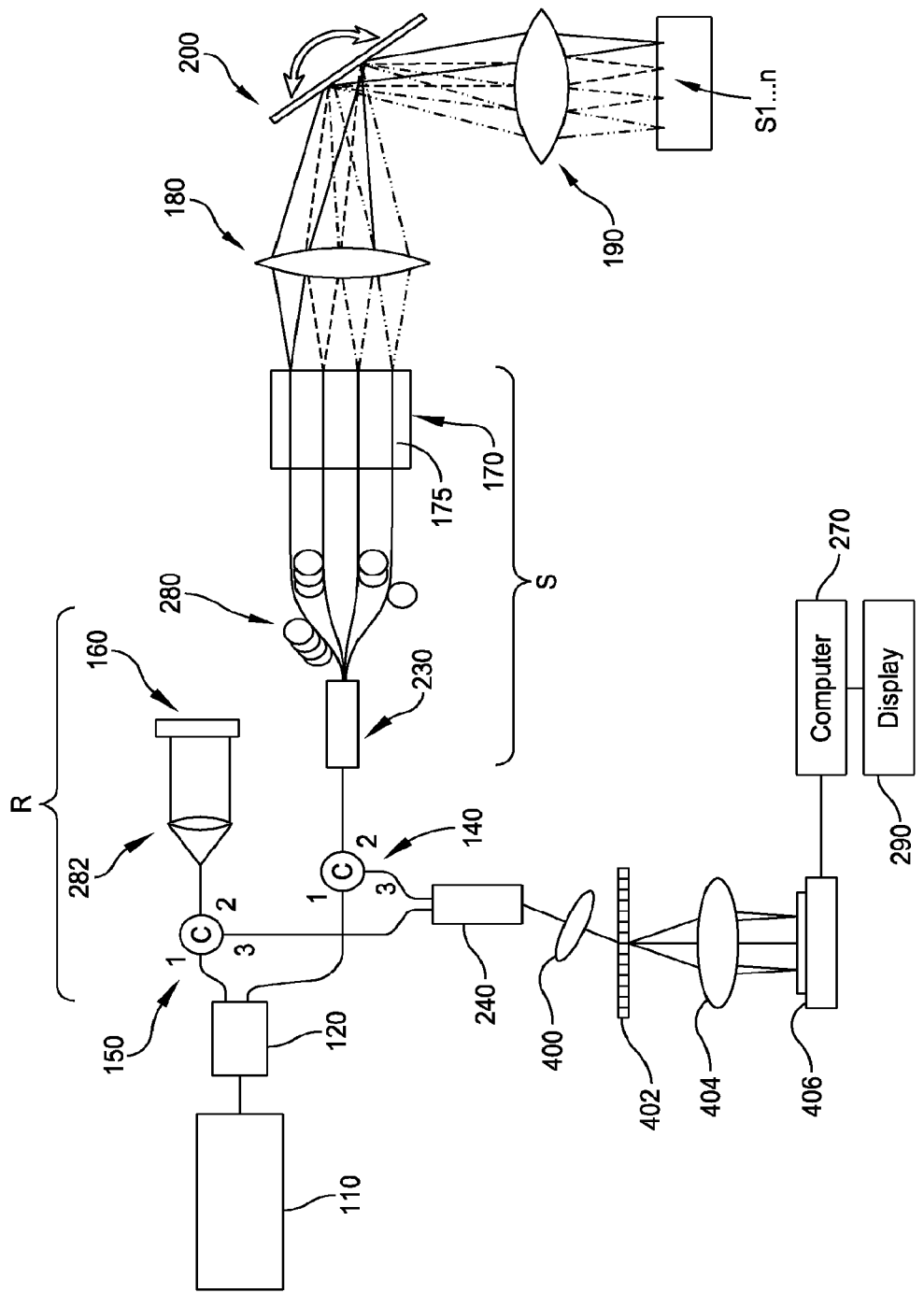
FIG. 15 is a schematic diagram of a spectral domain space-division multiplexing optical coherence tomography (SDM-OCT) system using a broadband light source.

FIG. 15 shows one embodiment of space-division multiplexing OCT (SDM-OCT) using spectral-domain methods. In this configuration, the light source 110 is a broadband light source with long coherence length for each individual wavelength. The detection system is basically a spectrometer. The spectrometer comprises a collimating lens 400, a grating 402, a focusing lens 404 and a line-scan camera 406 or 2D camera. The grating 402 splits the interference signal from the sample and reference arm S, R into different colors, which are focused by the focusing lens 404 onto different pixels on the line-scan or CCD cameras 406. High pixel count of the camera 406 allows long imaging range of the OCT system, which is desirable for simultaneous detection of signals from different optical delays.

Figure 16:
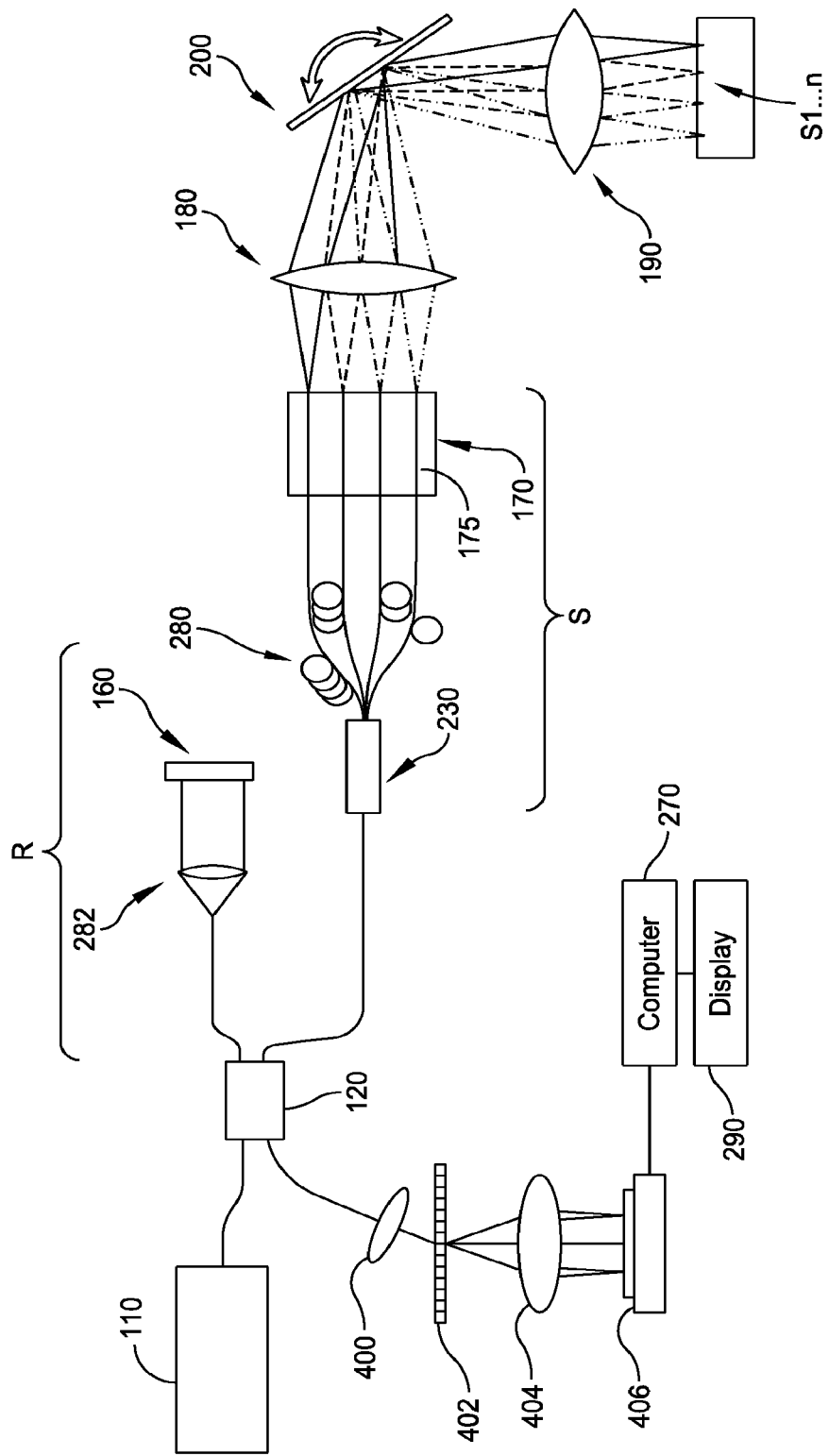
FIG. 16 is a schematic diagram of an alternative embodiment of a spectral domain space-division multiplexing optical coherence tomography (SDM-OCT) system using a broadband light source.

FIG. 16 shows another embodiment for spectral-domain SDM-OCT. In this configuration, output light from the broadband light source 110 is split into reference arm R and sample arm S directly at the first optical coupler 120 and the returned signal is combined using the same optical coupler before the signal was detected by the spectrometer. Similar configurations can be used for a wavelength tunable light (e.g. swept source laser) SS-OCT setup as well. This system configuration is simpler and appropriate for some applications, however; detection sensitivity of this setup may be lower compared to the configurations using optical circulators as in FIG. 15.

Figure 18:
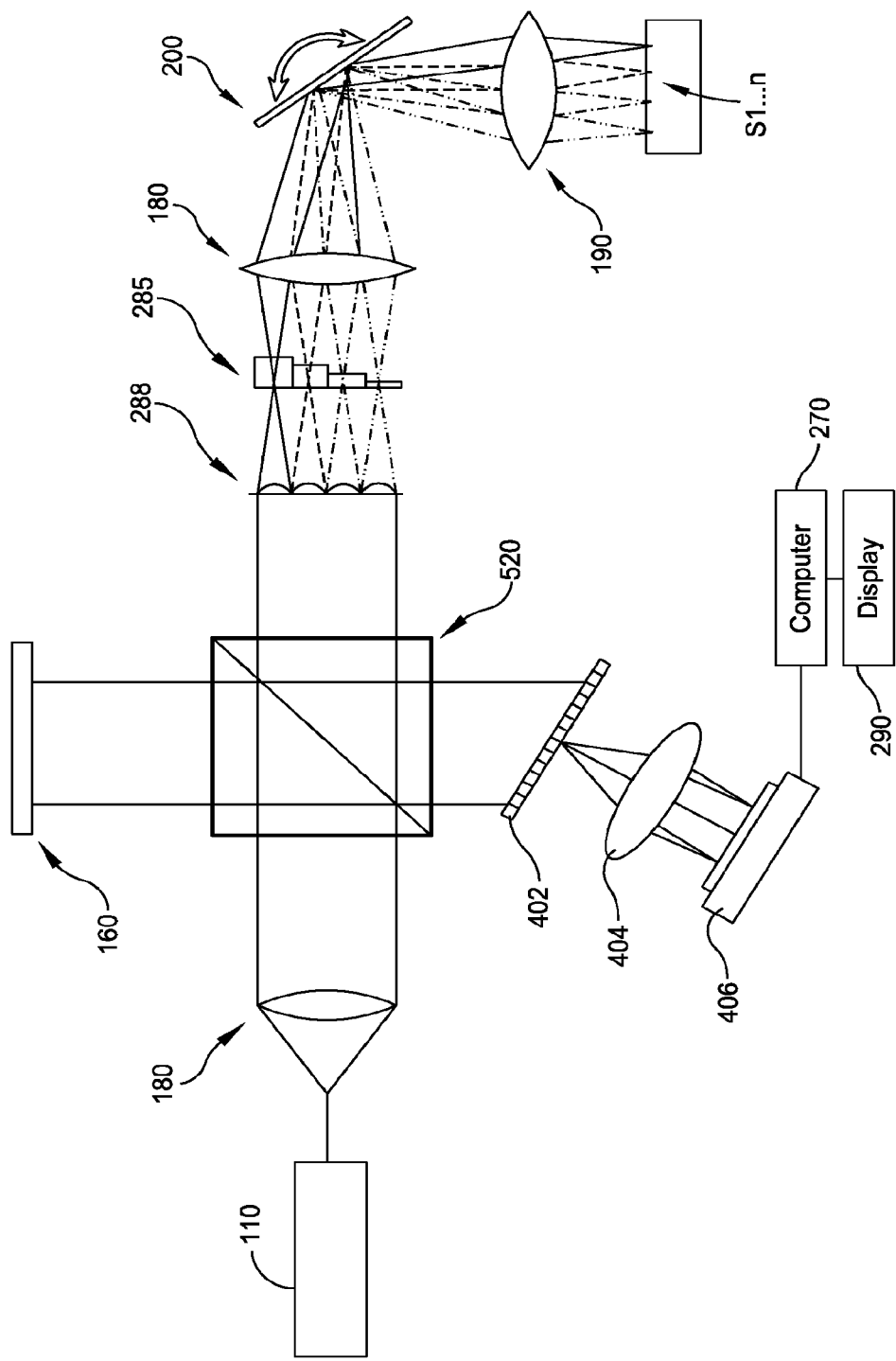
FIG. 18 is a schematic diagram of an alternative embodiment of a free-space light transmission space-division multiplexing optical coherence tomography (SDM-OCT) system.

FIG. 18 shows another embodiment for spectral-domain SDM-OCT using a free-space optical arrangement in lieu of optical fibers. In this configuration, output light from the broadband light source 110 is collimated and split into reference arm R and sample arm S directly at an appropriately configured first optical beam splitter 520 and the returned signal is combined using the same optical beam splitter before the signal is detected by the spectrometer. Similar configurations can be used for a wavelength tunable light (e.g. swept source laser) SS-OCT setup as well. This system configuration is simpler and appropriate for some applications. The detection sensitivity of this setup is high since there is no insertion loss within the optical system. Other components shown in FIG. 18 may be the same as the similarly numbered components in FIGS. 13 and 16.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An optical coherence tomography system with space-division multiplexing, the system comprising:
   a long coherence light source producing light having a coherence length greater than 5 mm to provide optimal imaging depth range;
   a first optical device configured to split the light into reference light and sampling light;
   a non-sweeping reference arm receiving the reference light and producing a reference light signal;
   a second optical device arranged on a sample arm and configured to split the sampling light into a plurality of sampling beams and transmit the plurality of sampling beams simultaneously;
   an optical delay element configured to produce an optical delay between the plurality of sampling beams;
   a scanner arranged to receive and configured to simultaneously scan the plurality of sampling beams onto multiple different sampling locations on a surface of a sample;
   the second optical device operable to simultaneously receive a plurality of reflected light signals returned from the multiple sampling locations;
   a third optical device configured to generate a plurality of interference signals based on simultaneously receiving the plurality of reflected light signals returned from the multiple sampling locations on the surface of the sample produced by the plurality of sampling beams and the reference light signal;
   wherein the interference signals includes data representing digitized images of all of the multiple sampling locations simultaneously from the sample.

2. The system of claim 1, wherein the first optical device is an optical coupler operable to divert the reference light to the reference arm and to divert the sampling light to the sample arm.

3. The system of claim 1, further comprising a single sample arm which includes the second optical device, the sample arm transmitting the plurality of sampling beams to the scanner.

4. The system of claim 1, wherein the second optical device is an optical fiber splitter.

5. The system of claim 4, wherein the optical splitter is planar lightwave circuit splitter.

6. The system of claim 1, wherein the second optical device is a microlens array.

7. The system of claim 6, wherein the optical delay element comprises a plurality of glass or plastic members each having a different thickness and receiving a portion of the sampling light from the microlens array.

8. The system of claim 1, further comprising a balanced detector arranged and operable to detect the interference signal.

9. The system of claim 1, wherein the optical delay element comprises an optical fiber array comprised of plurality of optical fibers each having a different length and conveying one of the plurality of sampling beams.

10. The system of claim 1, wherein the second optical device is further configured to combine the reflected light signals from the sample into a single detection signal containing the reflected light signals, the detection signal being transmitted to the at least one third optical device.

11. The system of claim 1, wherein the third optical device is an optical coupler.

12. The system of claim 1, wherein the light source is a wavelength tunable light source.

13. The system of claim 12, wherein the light source is a vertical-cavity surface-emitting laser diode.

14. The system of claim 1, further comprising a fourth optical device configured to divert a portion of the light to a Mach-Zehnder interferometer, the Mach-Zehnder interferometer configured and operable to clock acquisition of the reflected light signals returned from the surface of the sample.

15. The system of claim 1, further comprising a high speed data acquisition card and computer processor configured to capture and process the interference signal and generate a visual display of the actual images of the sample on a display device.

16. An optical coherence tomography system with space-division multiplexing, the system comprising:
   a long coherence light source producing light having a coherence length greater than 5 mm to provide optimal imaging depth range;
   a first optical coupler configured to divide the light into reference light and sampling light;
   a non-sweeping reference arm defining a first optical light path, the reference arm receiving the reference light and generating a reference light signal based on the reference light;
   a single sample arm defining a second optical light path and receiving the sampling light;
   an optical fiber splitter arranged on the sample arm and dividing the sampling light into a plurality of sampling light beams;
   an optical delay element comprising a plurality of optical fibers each having a different length and conveying one of the plurality of sampling light beams, the optical fibers producing an optical delay between the plurality of sampling beams;
   a scanner receiving and simultaneously scanning the plurality of sampling beams onto multiple different sampling locations on a surface of a sample;
   the optical fiber splitter operable to simultaneously receive a plurality of reflected light signals returned from the multiple sampling locations produced by each of the plurality of sampling beams;
   a second optical coupler receiving and combining the reference light signal and the plurality of reflected light signals each returned simultaneously from the multiple sampling locations on the surface of the sample produced by each of the plurality of sampling beams to produce a plurality of interference signals each associated with one of the plurality of reflected light signals;
   wherein the interference signals includes data representing digitized images of all of the multiple sampling locations simultaneously from the sample.

17. The system of claim 16, wherein the sampling light enters the optical splitter via a single optical fiber and each sampling beam exits the optical splitter via an optical fiber forming an array comprising a plurality of optical fibers.

18. The system of claim 17, wherein the optical splitter is planar lightwave circuit splitter.

19. The system of claim 16, further comprising a balanced detector operable to detect the interference signal.

20. The system of claim 16, wherein the light source is a wavelength tunable laser.

21. The system of claim 16, wherein the light source is a broadband light source.

22. A method for imaging a sample using a space-division multiplexing optical coherence tomography system, the method comprising:

providing an optical coherence tomography system comprising a long coherence light source producing light having a coherence length greater than 5 mm to provide optimal imaging depth range, a non-sweeping reference arm defining a first optical path, and a sample arm defining a second optical path;

dividing the light from the light source into reference light and sampling light;

transmitting the reference light to the reference arm to produce a reflected light signal;

transmitting the sampling light to the sample arm;

splitting the sampling light into a plurality of sampling beams on the sample arm;

producing an optical delay between the plurality of sampling beams;

simultaneously scanning the plurality of sampling beams onto a surface of a sample at multiple different sample locations;

collecting a plurality of reflected light signals each returned from the surface of the sample produced by each of the plurality of sampling beams;

combining the plurality of reflected light signals into a single reflected light signal comprised of the plurality of reflected light signals;

combining the single reflected light signal comprised of the plurality of reflected light signals and the reference light signal to produce a plurality of interference signals, the interference signals comprising data representing digitized images of all of the multiple different sample locations simultaneously from the sample.

23. The method of claim 22, wherein a single sample arm is provided.

24. The method of claim 22, wherein the splitting step is performed using an optical splitter.

25. The method of claim 22, further comprising detecting the interference signal using a balanced detector.

26. The method of claim 22, further comprising transmitting a portion of the light from the light source to a Mach-Zehnder interferometer to clock acquisition of the interference signal.

27. The method of claim 22, wherein the step of producing the optical delay includes transmitting each of the sampling beams in one of a plurality of optical fibers each having a different length.

* * * * *